US011236136B2

United States Patent
Wetter et al.

(10) Patent No.: US 11,236,136 B2
(45) Date of Patent: Feb. 1, 2022

(54) METHODS OF PRODUCING GLYCOSYLATED PROTEINS

(71) Applicants: LimmaTech Biologics AG, Schlieren (CH); Eidgenossische Technische Hochschule, Zurich (CH)

(72) Inventors: Michael L. Wetter, Zürich (CH); Michael T. Kowarik, Zürich (CH); Amirreza Faridmoayer, Zürich (CH); Manuela Mally, Watt (CH); Christian A. Lizak, Oberengstringen (CH); Markus Aebi, Wettingen (CH); Chia-wei Lin, Zürich (CH); Ivan Hang, Zürich (CH); Timothy Keys, Uster (CH)

(73) Assignees: LIMMATECH BIOLOGICS AG, Schlieren (CH); EIDGENÖSSISCHE TECHNISCHE HOCHSCHULE ZÜRICH, Zürich (CH)

(*) Notice: Subject to any disclaimer, the term of this patent is extended or adjusted under 35 U.S.C. 154(b) by 849 days.

(21) Appl. No.: 15/779,839

(22) PCT Filed: Nov. 30, 2016

(86) PCT No.: PCT/EP2016/079232
§ 371 (c)(1),
(2) Date: May 29, 2018

(87) PCT Pub. No.: WO2017/093291
PCT Pub. Date: Jun. 8, 2017

(65) Prior Publication Data
US 2018/0354997 A1    Dec. 13, 2018

Related U.S. Application Data

(60) Provisional application No. 62/260,725, filed on Nov. 30, 2015, provisional application No. 62/416,853, filed on Nov. 3, 2016.

(51) Int. Cl.
| | |
|---|---|
| A61K 39/00 | (2006.01) |
| C07K 14/285 | (2006.01) |
| C12N 9/10 | (2006.01) |
| C12P 19/04 | (2006.01) |
| C07K 16/22 | (2006.01) |
| C12N 9/12 | (2006.01) |
| C12P 21/00 | (2006.01) |
| A61K 38/00 | (2006.01) |

(52) U.S. Cl.
CPC ........... *C07K 14/285* (2013.01); *A61K 39/00* (2013.01); *C07K 16/22* (2013.01); *C12N 9/1048* (2013.01); *C12N 9/1051* (2013.01); *C12N 9/1241* (2013.01); *C12P 19/04* (2013.01); *C12P 21/005* (2013.01); *C12Y 207/07043* (2013.01); *A61K 38/00* (2013.01); *C07K 2318/00* (2013.01); *Y02A 50/30* (2018.01)

(58) Field of Classification Search
CPC .. C07K 14/285; C12N 9/1051; C12N 9/1048; C12N 9/1241; C12P 21/005
See application file for complete search history.

(56) References Cited

FOREIGN PATENT DOCUMENTS

| WO | 2005090552 A2 | | 9/2005 |
|---|---|---|---|
| WO | 2007101862 A1 | | 9/2007 |
| WO | 2013020988 | * | 2/2013 |
| WO | 2013020988 A1 | | 2/2013 |
| WO | 2014145180 A1 | | 9/2014 |

OTHER PUBLICATIONS

Lindhout et al: "Site-specific enzymatic polysialylation of therapeutic proteins using bacterial enzymes", Proceedings of the National Academy of Sciences, vol. 108, No. 18, May 3, 2011 (May 3, 2011), pp. 7397-7402, XP055077840, ISSN: 0027-8424, DOI: 10.1073/pnas.1019266108.
Schwarz et al: "Cytoplasmic N-Glycosyltransferase of Actinobacillus pleutopneumoniae Is an Inverting Enzyme and Recognizes the NX(S/T) Consensus Sequence", Journal of Biological Chemistry, vol. 286, No. 40, Oct. 7, 2011 (Oct. 7, 2011), pp. 35267-35274, XP55337795, ISSN: 0021-9258, DOI: 10.1074/jbc.M111.277160.
Naegeli et al: "Molecular Analysis of an Alternative N-Glycosylation Machinery by Functional Transfer from Actinobacillus pleuropneumoniae to *Escherichia coli*", Journal of Biological Chemistry, vol. 289, No. 4, Jan. 24, 2014 (Jan. 24, 2014), pp. 2170-2179, XP055337235, ISSN: 0021-9258, DOI: 10.1074/jbc.M113.524462.

* cited by examiner

*Primary Examiner* — Karen Cochrane Carlson
(74) *Attorney, Agent, or Firm* — Jones Day

(57) ABSTRACT

Described herein are methods of producing glycosylated proteins in vitro and in vivo. The methods include using host cells to produce glycosylated proteins. Also described herein are glycosylated proteins produced using such methods and uses thereof.

Figure 1:
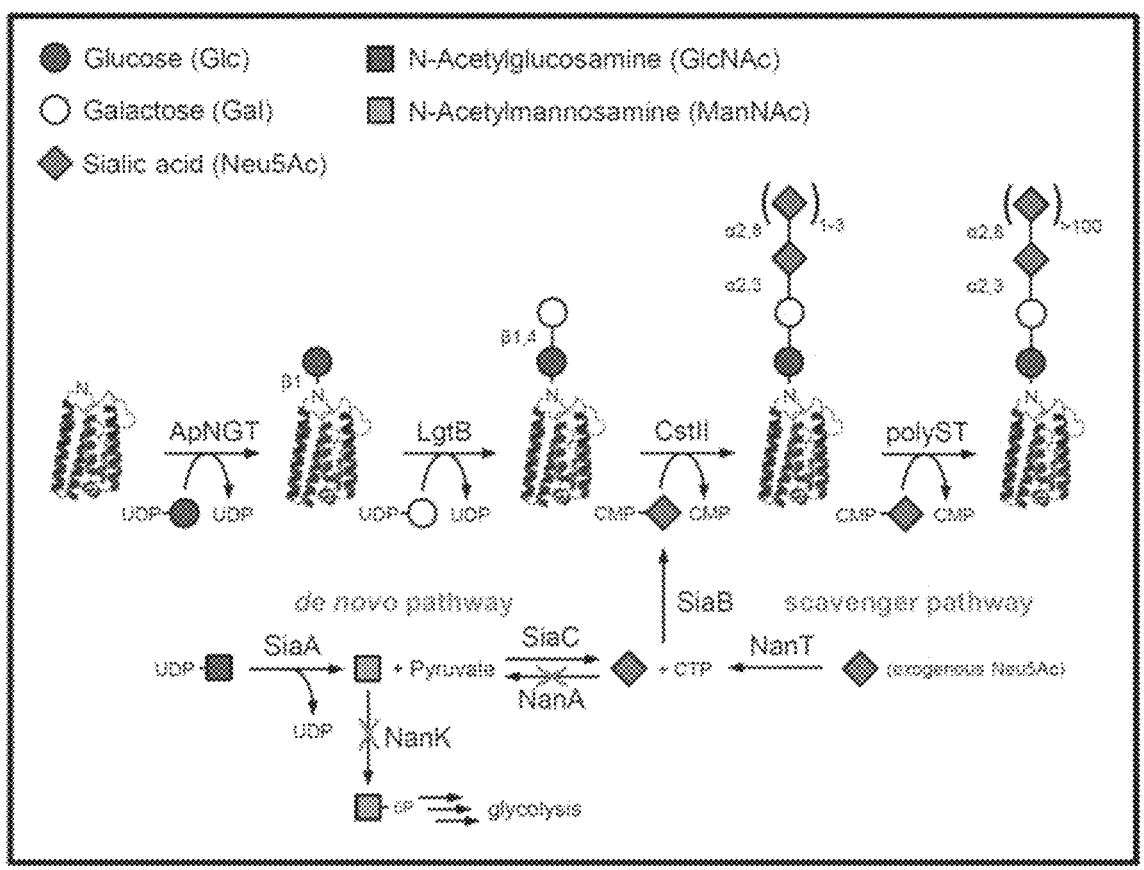

13 Claims, 11 Drawing Sheets
Specification includes a Sequence Listing.

SEQUENCE LISTING

```
<160> NUMBER OF SEQ ID NOS: 7

<210> SEQ ID NO 1
<211> LENGTH: 620
<212> TYPE: PRT
<213> ORGANISM: Artificial Sequence
<220> FEATURE:
<223> OTHER INFORMATION: ApNGT Sequence

<400> SEQUENCE: 1

Met Glu Asn Glu Asn Lys Pro Asn Val Ala Asn Phe Glu Ala Ala Val
1               5                   10                  15

Ala Val Lys Asp Tyr Glu Lys Ala Cys Ser Glu Leu Leu Leu Ile Leu
```

```
            20                  25                  30
Ser Gln Leu Asp Ser Asn Phe Gly Gly Ile Gln Glu Ile Glu Phe Glu
        35                  40                  45
Tyr Pro Val Gln Leu Gln Asp Leu Glu Gln Glu Lys Ile Val Tyr Phe
    50                  55                  60
Cys Thr Arg Met Ala Thr Ala Ile Thr Thr Leu Phe Ser Asp Pro Val
65                  70                  75                  80
Leu Glu Ile Ser Asp Leu Gly Val Gln Arg Phe Leu Val Tyr Gln Arg
                85                  90                  95
Trp Leu Ala Leu Ile Phe Ala Ser Ser Pro Phe Val Asn Ala Asp His
            100                 105                 110
Ile Leu Gln Thr Tyr Asn Arg Glu Pro Asn Arg Lys Asn Ser Leu Glu
        115                 120                 125
Ile His Leu Asp Ser Ser Lys Ser Ser Leu Ile Lys Phe Cys Ile Leu
    130                 135                 140
Tyr Leu Pro Glu Ser Asn Val Asn Leu Asn Leu Asp Val Met Trp Asn
145                 150                 155                 160
Ile Ser Pro Glu Leu Cys Ala Ser Leu Cys Phe Ala Leu Gln Ser Pro
                165                 170                 175
Arg Phe Ile Gly Thr Ser Thr Ala Phe Asn Lys Arg Ala Thr Ile Leu
            180                 185                 190
Gln Trp Phe Pro Arg His Leu Asp Gln Leu Lys Asn Leu Asn Asn Ile
        195                 200                 205
Pro Ser Ala Ile Ser His Asp Val Tyr Met His Cys Ser Tyr Asp Thr
    210                 215                 220
Ser Val Asn Lys His Asp Val Lys Arg Ala Leu Asn His Val Ile Arg
225                 230                 235                 240
Arg His Ile Glu Ser Glu Tyr Gly Trp Lys Asp Arg Tyr Val Ala His
                245                 250                 255
Ile Gly Tyr Arg Asn Asn Lys Pro Val Met Val Val Leu Glu His
            260                 265                 270
Phe His Ser Ala His Ser Ile Tyr Arg Thr His Ser Thr Ser Met Ile
        275                 280                 285
Ala Ala Arg Glu His Phe Tyr Leu Ile Gly Leu Gly Ser Pro Ser Val
    290                 295                 300
Asp Gln Ala Gly Gln Glu Val Phe Asp Glu Phe His Leu Val Ala Gly
305                 310                 315                 320
Asp Asn Met Lys Gln Lys Leu Glu Phe Ile Arg Ser Val Cys Glu Ser
                325                 330                 335
Asn Gly Ala Ala Ile Phe Tyr Met Pro Ser Ile Gly Met Asp Met Thr
            340                 345                 350
Thr Ile Phe Ala Ser Asn Thr Arg Leu Ala Pro Ile Gln Ala Ile Ala
        355                 360                 365
Leu Gly His Pro Ala Thr Thr His Ser Asp Phe Ile Glu Tyr Val Ile
    370                 375                 380
Val Glu Asp Asp Tyr Val Gly Ser Glu Ala Cys Phe Ser Glu Thr Leu
385                 390                 395                 400
Leu Arg Leu Pro Lys Asp Ala Leu Pro Tyr Val Pro Ser Ala Leu Ala
                405                 410                 415
Pro Glu Lys Val Asp Tyr Leu Leu Arg Glu Asn Pro Glu Val Val Asn
            420                 425                 430
Ile Gly Ile Ala Ser Thr Thr Met Lys Leu Asn Pro Tyr Phe Leu Glu
        435                 440                 445
```

Ala Leu Lys Ala Ile Arg Asp Arg Ala Lys Val Lys Val His Phe His
    450                 455                 460

Phe Ala Leu Gly Gln Ser Asn Gly Ile Thr His Pro Tyr Val Glu Arg
465                 470                 475                 480

Phe Ile Lys Ser Tyr Leu Gly Asp Ser Ala Thr Ala His Pro His Ser
                485                 490                 495

Pro Tyr His Gln Tyr Leu Arg Ile Leu His Asn Cys Asp Met Met Val
            500                 505                 510

Asn Pro Phe Pro Phe Gly Asn Thr Asn Gly Ile Ile Asp Met Val Thr
        515                 520                 525

Leu Gly Leu Val Gly Val Cys Lys Thr Gly Ala Glu Val His Glu His
    530                 535                 540

Ile Asp Glu Gly Leu Phe Lys Arg Leu Gly Leu Pro Glu Trp Leu Ile
545                 550                 555                 560

Ala Asn Thr Val Asp Glu Tyr Val Arg Ala Val Arg Leu Ala Glu
                565                 570                 575

Asn His Gln Glu Arg Leu Glu Leu Arg Arg Tyr Ile Ile Glu Asn Asn
            580                 585                 590

Gly Leu Asn Thr Leu Phe Thr Gly Asp Pro Arg Pro Met Gly Gln Val
        595                 600                 605

Phe Leu Glu Lys Leu Asn Ala Phe Leu Lys Glu Asn
    610                 615                 620

<210> SEQ ID NO 2
<211> LENGTH: 1863
<212> TYPE: DNA
<213> ORGANISM: Artificial Sequence
<220> FEATURE:
<223> OTHER INFORMATION: Wild type ApNGT

<400> SEQUENCE: 2
atggaaaacg aaataaaacc gaatgtagct aattttgaag cggcggttgc ggttaaagat      60
tatgaaaaag cttgctccga attacttttta attttgagtc agttagacag taactttggt     120
ggtattcagg agattgagtt tgaatatccg gtgcagcttc aggatttaga acaagaaaaa     180
atagtttatt tttgtacgcg tatggcaacg gcgattacta cgttgttttc cgatcctgtc     240
ttagaaatct ccgatttagg cgttcagaga ttttttggttt atcaacgttg gttagcgtta     300
atctttgcca gttcaccgtt tgtgaatgcg gatcatatat tacaaacata acagagag      360 ccgaatcgta agaatagttt agagattcat ttagattctt caaaatcgtc attaattaaa     420
ttctgtatcc tgtatttacc ggaatctaac gtaaatttga atctggatgt aatgtggaat     480
atttcacctg aattatgcgc ttcttttatgt tttgctttgc aatcgcctcg ttttatcggt     540
acatcaactg cgtttaataa acgagcgacc attttgcaat ggtttccacg acatttggat     600
caacttaaaa acctgaataa tattcctagt gccatttcgc atgacgtata tatgcattgt     660
agttatgata cgtcagtaaa taaacatgat gtgaaaaggg cgttaaatca tgttattcgt     720
cgccatatcg aaagtgaata cggttggaaa gatcgatatg tcgctcatat cggttatcgt     780
aataataaac cggttatggt cgtattactg gaacatttcc attcggccca ttctatttac     840
cgtacgcatt ccacatctat gattgcggcg cgtgaacatt tctatttaat cggtttaggt     900
agtccgtcgg ttgatcaagc gggtcaagag gtttttgatg agttccactt ggttgccggc     960
gataatatga agcagaagtt agaatttatc cgctcagttt gtgagagcaa cggtgccgca    1020 atatttttata tgccgagtat cggtatggat atgacgacga ttttcgcaag taatacgcgc    1080

-continued

```
cttgctccga tacaagcgat cgcattgggg catccggcaa caacacattc ggacttcatt    1140
gaatatgtga ttgtggaaga cgattatgtc ggctcggaag cgtgttttag tgaaacatta    1200
ttgcgcttac cgaaagacgc attaccttat gttccgtcag cattagcacc tgagaaggtg    1260
gattatttat tacgtgaaaa tccggaagtg gtaaatatcg gtatagcttc aaccacgatg    1320
aagctaaatc cgtatttctt agaagcgtta aaagcgattc gtgatcgtgc caaagtgaaa    1380
gtgcatttcc attttgcatt ggggcaatca acggtatta ctcacccgta tgtagaacgc     1440
tttattaaat cttatttagg tgattcggcc actgcgcacc ctcattctcc ttatcatcaa    1500
tatctccgta ttttgcataa ttgcgatatg atggtaaacc cgttcccatt cgggaatacg    1560
aacggaatta tcgatatggt cactttaggc ttagttggtg tgtgtaagac aggagccgaa    1620
gttcatgagc atattgatga agggctgttt aaacgtttag cttacccga gtggctgata     1680 gcaaatacgg tagatgaata tgttgaacgg gcggttcgct tagcggaaaa tcatcaggag    1740
cgtttagagt tacgtcgata tattattgaa aataacggat tgaacacatt gtttaccggg    1800
gatcctagac cgatgggaca gtattttta gaaaaattaa atgcgttcct aaaagaaaat     1860
taa                                                                 1863
```

<210> SEQ ID NO 3
<211> LENGTH: 1863
<212> TYPE: DNA
<213> ORGANISM: Artificial Sequence
<220> FEATURE:
<223> OTHER INFORMATION: Codon Optimized ApNGT

<400> SEQUENCE: 3

```
atggagaacg agaataagcc taatgttgca aactttgagg cggcagttgc tgtcaaagac      60
tacgagaagg cttgctccga gctgttgctg atcttgtctc agctggatag caactttggc     120
ggtattcaag aaatcgagtt cgagtacccg gttcaactcc aggacctcga acaagagaaa     180
attgtatact tctgcacccg catggcgacc gcgatcacga ccttgttttc cgaccctgtt     240
ctggagatca gcgacctggg tgttcagcgt ttcctggttt accaacgttg gctcgcattg     300
atctttgcat cgtccccgtt tgttaacgcg atcatattc tgcaaaccta taccgcgaa      360 ccgaaccgta aaactctttt ggaaatccat ctggactcta gcaaatccag cctcatcaaa    420
ttttgcattt tatacttgcc ggagtccaac gtcaacctga acttggacgt gatgtggaac    480
attagcccgg agttgtgcgc cagcctgtgc ttcgcactgc agtcgccgcg cttcatcggc    540
acctctaccg cgttcaacaa gcgtgcgact attttacaat ggtttccacg tcacctggac    600
cagctgaaaa atttgaacaa cattccgagc gcgatttccc acgacgtcta tatgcattgc    660
tcttacgaca cctccgtgaa caagcatgat gtcaaacgtg cgctgaacca tgtgattcgc    720
cgtcatatcg agtccgaata cggctggaaa gaccgttacg tggcgcacat cggctaccgt    780
aacaacaagc cggtgatggt tgttctgctg agcactttc actctgcaca ctccatctat      840
cgtacccact cgacctccat gattgcggcc cgcgagcact tttacctgat cggtttgggt    900
agcccgagcg ttgatcaagc gggccaagag gtttttgacg agtttcatct cgttgcgggt    960
gataatatga agcagaagct ggagttcatt cgttcggtgt gcgagtctaa cggtgccgcc   1020
atcttctaca tgccgtccat tggcatggat atgaccacca tcttcgcttc gaatactcgc   1080
cttgcgccta tccaggcgat cgcactgggc caccctgcca ccaccacag cgactttatc    1140 gagtacgtca tcgttgagga cgattacgtg ggctccgagg catgctttag cgaaacgttg   1200
```

```
ctgagactgc cgaaggacgc gctgccgtat gtcccgtccg ccttggcccc ggagaaagtt    1260
gattatcttt tgcgtgagaa tccagaggtc gttaatattg cattgcgag caccaccatg    1320 aagctgaacc cttatttctt ggaagcgctg aaggcgatcc gtgatcgtgc taaagtcaaa    1380
gttcacttcc attttgcgct gggccaaagc aacggtatta cccatccata cgttgagcgt    1440
ttcattaagt cctacctggg tgatagcgcg accgctcacc cacattcccc gtatcaccaa    1500
tacttgcgca tcttgcataa ttgcgacatg atggttaacc cgttcccgtt tggtaacacg    1560
aatggcatca ttgatatggt gaccctcggt ctggttggtg tttgcaaaac cggtgcagag    1620
gtccacgaac acatcgacga gggcttgttt aagcgtctgg gcttgccgga atggctgatt    1680
gccaacaccg ttgacgaata tgtggagcgt gcggtgcgtt tggcggaaaa ccaccaggaa    1740
cgcttggagc tgcgccgcta tattatcgag aataatggct tgaatacgct gtttaccggt    1800
gacccgcgtc cgatgggtca ggttttttctg gaaaaattga cgctttcttt gaaggagaac    1860
taa                                                                  1863
```

<210> SEQ ID NO 4
<211> LENGTH: 12
<212> TYPE: PRT
<213> ORGANISM: Artificial Sequence
<220> FEATURE:
<223> OTHER INFORMATION: tryptic peptide from scAtaC (Fig. 3)

<400> SEQUENCE: 4

Gly Asn Leu Ser Thr Ala Ala Asp Val Thr Asp Lys
1               5                   10

<210> SEQ ID NO 5
<211> LENGTH: 30
<212> TYPE: PRT
<213> ORGANISM: Artificial Sequence
<220> FEATURE:
<223> OTHER INFORMATION: Glyco-Tag-GFP

<400> SEQUENCE: 5

Lys Thr Ser Ala His Ala Thr Ala Ser Gly Ala His Ala Thr Ala Gly
1               5                   10                  15

Ser Ala Asn Ala Thr Ala Trp Ser His Pro Gln Phe Glu Lys
            20                  25                  30

<210> SEQ ID NO 6
<211> LENGTH: 15
<212> TYPE: PRT
<213> ORGANISM: Artificial Sequence
<220> FEATURE:
<223> OTHER INFORMATION: Glyco-Loop-GFP

<400> SEQUENCE: 6

Leu Ser Gly Ser Gly Ala Asn Ala Thr Ala Thr Gly Ser Gly Leu
1               5                   10                  15

<210> SEQ ID NO 7
<211> LENGTH: 33
<212> TYPE: PRT
<213> ORGANISM: Artificial Sequence
<220> FEATURE:
<223> OTHER INFORMATION: Tryptic peptide

<400> SEQUENCE: 7

Asp Gly Pro Val Leu Ser Gly Ser Gly Ala Asn Ala Thr Ala Thr Gly
1               5                   10                  15

```
Ser Gly Leu Pro Asp Asn His Tyr Leu Ser Thr Gln Ser Val Leu Ser
            20                  25                  30
Lys
```

METHODS OF PRODUCING GLYCOSYLATED PROTEINS

This application is a U.S. National Stage Application under 35 U.S.C. § 371 of International Patent Application No. PCT/EP2016/079232, filed Nov. 30, 2016, which claims priority benefit of U.S. Provisional Patent Application No. 62/260,725, filed Nov. 30, 2015, and U.S. Provisional Patent Application No. 62/416,853, filed Nov. 3, 2016, the contents of each of which are incorporated herein by reference in their entireties.

1. INTRODUCTION

Described herein are methods of producing glycosylated proteins in vitro and in vivo. The methods include using host cells to produce glycosylated proteins. Also described herein are glycosylated proteins produced using such methods and uses thereof.

2. BACKGROUND

Glycosylation is the most prominent posttranslational modification of secretory proteins in eukaryotes. In vivo synthesis of glycoproteins with defined structure remains a major hurdle to the understanding and exploitation of their biological activities and engineered glycosylation of recombinant proteins holds great potential for the development of novel therapeutic reagents and research tools. Available strategies known in the art for N-glycoprotein synthesis include arduous chemical synthesis and biosynthesis via the classical N-glycosylation pathway in eukaryotic or prokaryotic organisms. There remains a need in the art for new and improved systems of protein glycosylation, particularly host cells capable of producing glycosylated proteins in vivo.

3. SUMMARY

The instant application describes a platform for bottom-up synthesis of N-linked glycans directly in a host cell (e.g., bacterial), e.g., in the cytoplasm of a host cell, using an artificial biosynthetic pathway, consisting of glycosyltransferases (e.g., prokaryotic glycosyltransferases), which catalyze modification of a target protein (e.g., site-specific modification on a recombinant target protein). The N-glycosylation platform described herein does not require use of oligosaccharyltransferases or chemical coupling to achieve glycosylation of proteins (e.g., host cell expressed recombinant proteins). Instead, the biosynthetic pathway described herein uses an N-glycosyltransferase (NGT) to transfer a monosaccharide directly to an N-glycosylation consensus sequence of a target protein. Additional monosaccharides are then directly added to the N-linked monosaccharide thereby generating N-linked glycosylation directly on the target protein without the need of an oligosaccharyltransferase or chemical coupling.

N-glycosyltransferases (NGT) are capable of adding a glucose to an amino acid present in an N-glycosylation consensus sequence. For example, NGTs can N-glycosylate the asparagine (Asn) residue present in the N-glycosylation consensus sequence Asn-X-Ser(Thr), wherein X can be any amino acid except Pro. NGTs also can N-glycosylate other N-glycosylation consensus sequences. See Section 5.1. As disclosed herein, it has been discovered by the inventors that when a monosaccharide, e.g., galactose, is linked to the glucose added by the NGT, the resulting Asn-glucose-monosaccharide (e.g., galactose) can serve as a primer for synthesis of oligosaccharides/polysaccharides, resulting in the production of glycosylated proteins. This discovery allows for the glycosylation of proteins of choice, including peptides and polypeptides, collectively referred to herein as "target proteins," either in vivo or in vitro. In particular, various glycosyltransferases can be selected and combined with an NGT and a target protein that comprises one or more N-glycosylation consensus sequences, resulting in (i) glucosylation (addition of a glucose) to the asparagine (Asn) (or other relevant residue) in the consensus sequence; (ii) linkage of a monosaccharide (e.g., galactose) to the glucose; and (iii) assembly of an oligosaccharide or polysaccharide on the glucose-monosaccharide primer. In addition, various enzymes that generate precursors for glycosylation (e.g., CMP-Neu5Ac synthetases such as SynB) can be selected and combined with an NGT, target protein, and said various glycosyltransferases. Therefore, provided herein are methods of producing glycosylated target proteins, said methods comprising (i) using an NGT to add a glucose to a target protein that comprises one or more N-glycosylation consensus sequences; (ii) using a glycosyltransferase (e.g., a galactosyltransferase) to add a monosaccharide (e.g., galactose) to said glucose; and (iii) using one or more additional glycosyltransferases to generate an oligosaccharide or polysaccharide on the glucose-monosaccharide primer.

Importantly, it has been discovered that the system of N-glycosylation described herein can be incorporated into host cells, resulting in production of glycosylated target proteins in the cytoplasm of the host cells. Accordingly, in one aspect, provided herein are host cells capable of producing glycosylated proteins, e.g., N-glycosylated proteins. The host cells provided herein comprise, inter alia, (i) a nucleic acid that encodes an N-glycosyltransferase (NGT) that is capable of adding a glucose to the Asn residue (or other relevant residue) present in an N-glycosylation consensus sequence and (ii) a nucleic acid that encodes a glycosyltransferase that catalyzes addition of a monosaccharide, e.g., galactose, to the glucose added by the NGT. The host cells provided herein provide a novel system for protein glycosylation in vivo, wherein glycosylated proteins are produced in the cytoplasm of the host cells. Importantly, the host cells provided herein circumvent the need to produce glycosylated proteins in the periplasm, a limitation of currently existing in vivo glycosylation platforms.

In a specific embodiment, provided herein is a method for producing a glycosylated recombinant target protein in a host cell, wherein said method does not comprise use of an oligosaccharyltransferase (OST) or chemical coupling in said cell.

In another specific embodiment, provided herein is a method for producing a glycosylated target protein in a host cell, wherein said method comprises culturing a cell comprising a nucleotide sequence encoding the target protein and a nucleotide sequence encoding an NGT. In certain embodiments, such a host cell comprises further nucleotide sequences encoding one or more additional glycosyltransferases.

In certain embodiments, such a nucleotide sequence encoding a target protein comprises an N-glycosylation consensus sequence (e.g., Asn-X-Ser(Thr), wherein X can be any amino acid except Pro). In specific embodiments, the N-glycosylation consensus sequence is endogenous to the target protein. In other specific embodiments, the N-glycosylation consensus sequence is heterologous to the target protein. In certain embodiments, the consensus sequence is embedded in a heterologous sequence such that a heterologous sequence that comprises the N-glycosylation consensus sequence is added to the target protein. In specific embodiments, the heterologous sequence that comprises the N-glycosylation consensus sequence is added to the N or the C terminus or both, N and C terminus, of the target protein, wherein the heterologous sequence that comprises the N-glycosylation consensus sequence is defined as a terminal glycosylation tag. In other specific embodiments, the heterologous sequence that comprises the N-glycosylation consensus sequence is introduced or inserted anywhere in the primary structure of the protein, wherein the heterologous sequence that comprises the N-glycosylation consensus sequence is defined as an embedded glycosylation tag. In certain embodiments, the said terminal glycosylation tag or embedded glycosylation tag is at the surface of the otherwise folded target protein. In certain embodiments, the said terminal glycosylation tag or said embedded glycosylation tag is not part of the three-dimensional conformation of the target protein but remains unfolded. See Section 5.1.

In another specific embodiment, such a host cell further comprises nucleotide sequences encoding proteins capable of synthesizing one or more saccharide substrates for NGT and/or other glycosyltransferases (e.g., proteins capable of synthesizing UDP-glucose). In specific embodiments, said proteins comprise a CMP-Neu5Ac synthetase. In another specific embodiment, said CMP-Neu5Ac synthetase is SynB. In other embodiments, said nucleotide sequences encode UDP-N-acetylglucosamine 2-epimerase or sialic acid synthase.

In a specific embodiment, provided herein is a host cell comprising (i) a nucleic acid that encodes a target protein comprising an N-glycosylation consensus sequence; (ii) a nucleic acid that encodes an N-glycosyltransferase (NGT) that adds glucose to the Asn residue (or other relevant residue) present in said N-glycosylation consensus sequence, and (iii) a nucleic acid that encodes a glycosyltransferase that catalyzes addition of a monosaccharide to said glucose. In a specific embodiment, said target protein is heterologous to the host cell. In another specific embodiment, said NGT is heterologous to the host cell. In another specific embodiment, said glycosyltransferase that catalyzes addition of a monosaccharide to said glucose is heterologous to the host cell. In another specific embodiment, each of said target protein, said NGT and said glycosyltransferase that catalyzes addition of a monosaccharide to said glucose are heterologous to the host cell. In another specific embodiment, said host cell is *E. coli*.

In another specific embodiment, provided herein is a host cell comprising (i) a nucleic acid that encodes a target protein comprising an N-glycosylation consensus sequence; (ii) a nucleic acid that encodes an N-glycosyltransferase (NGT) that adds glucose to the Asn residue (or other relevant residue) present in said N-glycosylation consensus sequence, (iii) a nucleic acid that encodes a glycosyltransferase that catalyzes addition of a monosaccharide to said glucose; and (iv) a nucleic acid that encodes a sialyltransferase. In a specific embodiment, said sialyltransferase adds one or more sialic acid residues to said galactose. In another specific embodiment, said target protein is heterologous to the host cell. In another specific embodiment, said NGT is heterologous to the host cell. In another specific embodiment, said glycosyltransferase that catalyzes addition of a monosaccharide to said glucose is heterologous to the host cell. In another specific embodiment, said sialyltransferase is heterologous to the host cell. In another specific embodiment, each of said target protein, said NGT, said sialyltransferase, and said glycosyltransferase that catalyzes addition of a monosaccharide to said glucose are heterologous to the host cell. In another specific embodiment, said host cell is *E. coli*.

In another specific embodiment, provided herein is a host cell comprising (i) a nucleic acid that encodes a target protein comprising an N-glycosylation consensus sequence; (ii) a nucleic acid that encodes an N-glycosyltransferase (NGT) that adds glucose to the Asn residue present (or other relevant residue) in said N-glycosylation consensus sequence, (iii) a nucleic acid that encodes a glycosyltransferase that catalyzes addition of a monosaccharide to said glucose; (iv) a nucleic acid that encodes a sialyltransferase; and (v) a nucleic acid that encodes a polysialyltransferase (polyST). In a specific embodiment, said sialyltransferase adds one or more sialic acid residues to said galactose and said polyST synthesizes polysialic acid, allowing for production of polysialylated proteins with improved pharmacokinetic properties by said host cell. In another specific embodiment, said target protein is heterologous to the host cell. In another specific embodiment, said NGT is heterologous to the host cell. In another specific embodiment, said glycosyltransferase that catalyzes addition of a monosaccharide to said glucose is heterologous to the host cell. In another specific embodiment, said sialyltransferase is heterologous to the host cell. In another specific embodiment, said polyST is heterologous to the host cell. In another specific embodiment, each of said target protein, said NGT, said sialyltransferase, said polyST, and said glycosyltransferase that catalyzes addition of a monosaccharide to said glucose are heterologous to the host cell. In another specific embodiment, said host cell is *E. coli*.

In another specific embodiment, provided herein is a host cell comprising (i) a nucleic acid that encodes a target protein comprising an N-glycosylation consensus sequence; (ii) a nucleic acid that encodes an N-glycosyltransferase (NGT) that adds glucose to the Asn residue (or other relevant residue) present in said N-glycosylation consensus sequence, (iii) a nucleic acid that encodes a glycosyltransferase that catalyzes addition of a monosaccharide to said glucose; (iv) a nucleic acid that encodes a sialyltransferase; (v) a nucleic acid that encodes a polysialyltransferase (polyST); and (vi) a nucleic acid that encodes a CMP-Neu5Ac synthetase. In a specific embodiment, said sialyltransferase adds one or more sialic acid residues to said galactose and said polyST synthesizes polysialic acid, allowing for production of polysialylated proteins with improved pharmacokinetic properties by said host cell. In another specific embodiment, said target protein is heterologous to the host cell. In another specific embodiment, said NGT is heterologous to the host cell. In another specific embodiment, said glycosyltransferase that catalyzes addition of a monosaccharide to said glucose is heterologous to the host cell. In another specific embodiment, said sialyltransferase is heterologous to the host cell. In another specific embodiment, said polyST is heterologous to the host cell. In another specific embodiment, said CMP-Neu5Ac synthetase is heterologous to the host cell. In another specific embodiment, each of said target protein, said NGT, said sialyltransferase, said polyST, said CMP-Neu5Ac synthetase, and said glycosyltransferase that catalyzes addition of a monosaccharide to said glucose are heterologous to the host cell. In another specific embodiment, said host cell is *E. coli*.

In a specific embodiment, the host cells provided herein comprise a nucleic acid that encodes the NGT of a species of *Actinobacillus*. In a specific embodiment, said NGT is the NGT of *Actinobacillus pleuropneumoniae* (SEQ ID NO:1, amino acid sequence; see Table 2). See, e.g., Choi et al., PLoS ONE (2010). In another specific embodiment, said NGT is the NGT of *Actinobacillus suis, Actinobacillus succinogenes, Actinobacillus minor,* or *Actinobacillus capsulatus.*

In another specific embodiment, the host cells provided herein comprise a nucleic acid that encodes the NGT of a species of *Haemophilus,* e.g., *Haemophilus aegyptius, Haemophilus ducreyi, Haemophilus haemolyticus, Haemophilus influenza, Haemophilus parainfluenzae, Haemophilus parahaemolyticus, Haemophilus pittmaniae,* or *Haemophilus sputorum.*

In another specific embodiment, the host cells provided herein comprise a nucleic acid that encodes the NGT of a species of *Mannheimia,* e.g., *Mannheimia granulomatis, Mannheimia haemolytica, Mannheimia succiniproducens,* or *Mannheimia varigena.*

In another specific embodiment, the host cells provided herein comprise a nucleic acid that encodes the NGT of a species of *Bibersteinia,* e.g., *Bibersteinia trehalosi.*

In another specific embodiment, the host cells provided herein comprise a nucleic acid that encodes the NGT of a species of *Yersinia,* e.g., *Yersinia bercovieri, Yersinia enterocolitica, Yersinia frederiksenii, Yersinia intermedia, Yersinia kristensii, Yersinia mollaretii, Yersinia pestis, Yersinia pseudotuberculosis, Yersinia rhodei,* or *Yersinia similis.*

In certain embodiments, the NGT used in the host cells provided herein is one that is homologous to the NGT of any one of *Actinobacillus* (e.g., the NGT of *Actinobacillus pleuropneumoniae*), *Haemophilus, Mannheimia, Bibersteinia,* or *Yersinia.* For example, a host cell provided herein may comprise a nucleic acid that is about 70%, 75%, 80%, 85%, 90%, 95%, 96%, 97%, 98%, or 99% homologous to the nucleic acid that encodes an NGT of *Actinobacillus* (e.g., the NGT of *Actinobacillus pleuropneumoniae*), *Haemophilus, Mannheimia, Bibersteinia,* or *Yersinia.*

In certain embodiments, the nucleic acid that encodes a glycosyltransferase that catalyzes addition of a monosaccharide to said glucose present in the host cells provided herein encodes a galactosyltransferase. In a specific embodiment, said galactosyltransferase is the LgtB of a species of *Neisseria.* In a specific embodiment, said galactosyltransferase is LgtB of *N. meningitidis.* In another specific embodiment, said galactosyltransferase is LgtB of *N. gonorrhoeae.* In another specific embodiment, said galactosyltransferase is LgtE of *N. meningitidis.* In another specific embodiment, said galactosyltransferase is CgtB of *C. jejuni.* In another specific embodiment, said galactosyltransferase is WaaX of *E. coli.* In another specific embodiment, said galactosyltransferase is HP0826 of *Helicobacter pylori* In another specific embodiment, said galactosyltransferase is a eukaryotic β4Gal-T1.

In certain embodiments, the galactosyltransferase used in the host cells provided herein is one that is homologous to a galactosyltransferase of *Neisseria, Campylobacter, E. coli, Helicobacter pylori,* or a eukaryotic galactosyltransferase. For example, a host cell provided herein may comprise a nucleic acid that is about 70%, 75%, 80%, 85%, 90%, 95%, 96%, 97%, 98%, or 99% homologous to a nucleic acid that encodes an LgtB of a species of *Neisseria* (e.g., LgtB of *N. meningitidis,* LgtB of *N. gonorrhoeae,* or LgtE of *N. meningitidis*); about 70%, 75%, 80%, 85%, 90%, 95%, 96%, 97%, 98%, or 99% homologous to the nucleic acid that encodes CgtB of *C. jejuni*; about 70%, 75%, 80%, 85%, 90%, 95%, 96%, 97%, 98%, or 99% homologous to the nucleic acid that encodes WaaX of *E. coli*; about 70%, 75%, 80%, 85%, 90%, 95%, 96%, 97%, 98%, or 99% homologous to the nucleic acid that encodes HP0826 of *Helicobacter pylori*; or about 70%, 75%, 80%, 85%, 90%, 95%, 96%, 97%, 98%, or 99% homologous to the nucleic acid that encodes eukaryotic β4Gal-T1.

In another specific embodiment, when the host cells provided herein comprise a nucleic acid that encodes a sialyltransferase, said sialyltransferase from a species of *Campylobacter.* In a specific embodiment, said sialyltransferase is CstII of *C. jejuni.* In another specific embodiment, said sialyltransferase is CstI of *C. jejuni.* In another specific embodiment, said sialyltransferase is Lst of *N. meningitidis.* In another specific embodiment, said sialyltransferase is Lst of *N. gonorrhoeae.*

In certain embodiments, the sialyltransferase used in the host cells provided herein is one that is homologous to a sialyltransferase of *Neisseria* or *Campylobacter.* For example, a host cell provided herein may comprise a nucleic acid that is about 70%, 75%, 80%, 85%, 90%, 95%, 96%, 97%, 98%, or 99% homologous to the nucleic acid that encodes CstII of *C. jejuni,* CstI of *C. jejuni,* Lst of *N. meningitidis,* or Lst of *N. gonorrhoeae.*

In another specific embodiment, when the host cells provided herein comprise a nucleic acid that encodes a polysialyltransferase (polyST), said polyST is a polyST of *N. meningitidis.* In a specific embodiment, said polyST of *N. meningitidis* is a polyST of *N. meningitidis* serogroup B.

In another specific embodiment, when the host cells provided herein comprise a nucleic acid that encodes a polysialyltransferase (polyST), said polyST is a polyST of *E. coli* K1, *Mannheimania haemolytica,* or *Moraxella nonliquifacien.*

In certain embodiments, the polysialyltransferase used in the host cells provided herein is one that is homologous to a polysialyltransferase of a species of *Neisseria,* a species of *Mannheimania,* a species of *Moraxella,* or *E. coli.* For example, a host cell provided herein may comprise a nucleic acid that is about 70%, 75%, 80%, 85%, 90%, 95%, 96%, 97%, 98%, or 99% homologous to the nucleic acid that encodes the polyST of *N. meningitidis* serogroup B, the polyST of *Mannheimania haemolytica,* the polyST of *Moraxella nonliquifacien,* or the polyST of *E. coli.*

In another specific embodiment, when the host cells provided herein comprise a nucleic acid that encodes a CMP-Neu5Ac synthetase, said CMP-Neu5Ac synthetase is SynB of *N. meningitidis.* In another specific embodiment, host cells provided herein that comprise a nucleic acid that encodes a CMP-Neu5Ac synthetase are incubated with CMP-Neu5Ac synthetase substrates (e.g., sialic acid).

In certain embodiments, the CMP-Neu5Ac synthetase used in the host cells provided herein is one that is homologous to a CMP-Neu5Ac synthetase of a species of *Neisseria.* For example, a host cell provided herein may comprise a nucleic acid that is about 70%, 75%, 80%, 85%, 90%, 95%, 96%, 97%, 98%, or 99% homologous to the nucleic acid that encodes SynB of *N. meningitidis.*

In certain embodiments, the host cells provided herein are prokaryotic host cells. Exemplary prokaryotic host cells include, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell used herein is *E. coli.*

In certain embodiments, the host cells provided herein are eukaryotic host cells. Exemplary eukaryotic host cells include, without limitation, yeast cells, plant cells, insect cells, kinetoplastida cells, and mammalian cells.

In certain embodiments, the nucleic acid that encodes a target protein present in the host cells provided herein encodes a therapeutic protein, i.e., a protein used in the treatment of a disease or disorder. For example, the nucleic acid that encodes a target protein present in the host cells provided herein can encode an enzyme, a cytokine, a receptor, a ligand, a growth factor, a protein that acts as an inhibitor, or an antibody. A non-limiting list of target proteins is provided in Section 5.4, below.

In certain embodiments, the nucleic acid that encodes a target protein present in the host cells provided herein does not encode a GFP.

In another aspect, provided herein is a method for producing glycosylated target proteins, said method comprising (i) culturing a host cell provided herein under conditions suitable for protein production and (ii) isolating said target protein. In a specific embodiment, said host cell comprises (a) a nucleic acid that encodes a target protein comprising an N-glycosylation consensus sequence; (b) a nucleic acid that encodes an N-glycosyltransferase (NGT) that adds glucose to the Asn residue (or other relevant residue) present in said N-glycosylation consensus sequence, and (c) a nucleic acid that encodes a glycosyltransferase that catalyzes addition of a monosaccharide to said glucose, wherein at least one, two, or all of said target protein, said NGT, and said glycosyltransferase that catalyzes addition of a monosaccharide to said glucose are heterologous to the host cell. In another specific embodiment, said host cell is *E. coli*. In another specific embodiment, said NGT is the NGT of *Actinobacillus pleuropneumoniae*. In another specific embodiment, said nucleic acid that encodes a glycosyltransferase that catalyzes addition of a monosaccharide to said glucose present in the host cells provided herein encodes a galactosyltransferase, e.g., LgtB of *N. meningitidis*.

In another specific embodiment, provided herein is a method for producing sialylated target proteins with improved pharmacokinetic properties, said method comprising (i) culturing a host cell provided herein under conditions suitable for protein production and (ii) isolating said target protein. In a specific embodiment, said host cell comprises (a) a nucleic acid that encodes a target protein comprising an N-glycosylation consensus sequence; (b) a nucleic acid that encodes an N-glycosyltransferase (NGT) that adds glucose to the Asn residue (or other relevant residue) present in said N-glycosylation consensus sequence, (c) a nucleic acid that encodes a glycosyltransferase that catalyzes addition of a monosaccharide to said glucose; and (d) a nucleic acid that encodes a sialyltransferase, wherein one, two, three, or all of said target protein, said NGT, said sialyltransferase, and said glycosyltransferase that catalyzes addition of a monosaccharide to said glucose are heterologous to the host cell. In another specific embodiment, said host cell is *E. coli*. In another specific embodiment, said NGT is the NGT of *Actinobacillus pleuropneumoniae*. In another specific embodiment, said nucleic acid that encodes a glycosyltransferase that catalyzes addition of a monosaccharide to said glucose present in the host cells provided herein encodes a galactosyltransferase, e.g., LgtB of *N. meningitidis*. In another specific embodiment, said sialyltransferase is CstII of *C. jejuni*.

In another specific embodiment, provided herein is a method for producing polysialylated target proteins with improved pharmacokinetic properties, said method comprising (i) culturing a host cell provided herein under conditions suitable for protein production and (ii) isolating said target protein. In a specific embodiment, said host cell comprises (a) a nucleic acid that encodes a target protein comprising an N-glycosylation consensus sequence; (b) a nucleic acid that encodes an N-glycosyltransferase (NGT) that adds glucose to the Asn residue (or other relevant residue) present in said N-glycosylation consensus sequence, (c) a nucleic acid that encodes a glycosyltransferase that catalyzes addition of a monosaccharide to said glucose; (d) a nucleic acid that encodes a sialyltransferase; and (e) a nucleic acid that encodes a polysialyltransferase (polyST). In a specific embodiment, one, two, three, four, or all of said target protein, said NGT, said sialyltransferase, said polyST, and said glycosyltransferase that catalyzes addition of a monosaccharide to said glucose are heterologous to the host cell. In another specific embodiment, said host cell is *E. coli*. In another specific embodiment, said NGT is the NGT of *Actinobacillus pleuropneumoniae*. In another specific embodiment, said nucleic acid that encodes a glycosyltransferase that catalyzes addition of a monosaccharide to said glucose present in the host cells provided herein encodes a galactosyltransferase, e.g., LgtB of *N. meningitidis*. In another specific embodiment, said sialyltransferase is CstII of *C. jejuni*. In another specific embodiment, said polyST is a polyST of *N. meningitidis* (e.g., the polyST of *N. meningitidis* serogroup B).

In another specific embodiment, provided herein is a method for producing polysialylated target proteins, said method comprising (i) culturing a host cell provided herein under conditions suitable for protein production and (ii) isolating said target protein. In a specific embodiment, said host cell comprises (a) a nucleic acid that encodes a target protein comprising an N-glycosylation consensus sequence; (b) a nucleic acid that encodes an N-glycosyltransferase (NGT) that adds glucose to the Asn residue (or other relevant residue) present in said N-glycosylation consensus sequence, (c) a nucleic acid that encodes a glycosyltransferase that catalyzes addition of a monosaccharide to said glucose; (d) a nucleic acid that encodes a sialyltransferase; (e) a nucleic acid that encodes a polysialyltransferase (polyST); and (f) a nucleic acid that encodes a CMP-Neu5Ac synthetase. In a specific embodiment, one, two, three, four, five, or all of said target protein, said NGT, said sialyltransferase, said polyST, said CMP-Neu5Ac synthetase, and said glycosyltransferase that catalyzes addition of a monosaccharide to said glucose are heterologous to the host cell. In another specific embodiment, said host cell is *E. coli*. In another specific embodiment, said NGT is the NGT of *Actinobacillus pleuropneumoniae*. In another specific embodiment, said nucleic acid that encodes a glycosyltransferase that catalyzes addition of a monosaccharide to said glucose present in the host cells provided herein encodes a galactosyltransferase, e.g., LgtB of *N. meningitidis*. In another specific embodiment, said sialyltransferase is CstII of *C. jejuni*. In another specific embodiment, said polyST is a polyST of *N. meningitidis* (e.g., the polyST of *N. meningitidis* serogroup B). In another specific embodiment, said CMP-Neu5Ac synthetase is SynB of *N. meningitidis*.

In certain embodiments, when the host cells provided herein are used to produce sialylated and/or polysialylated proteins, the host cells are cultured in medium supplemented with N-Acetylneuraminic acid (Neu5Ac). See Antoine et al. Chem. Bio. Chem. 4, 406-412 (2003).

In certain embodiments, the target protein produced by the host cells provided is a therapeutic protein, i.e., a protein used in the treatment of a disease or disorder. For example, the target protein produced by the host cells provided herein can be an enzyme, a cytokine, or an antibody, wherein said target protein has been glycosylated, e.g., sialylated. A non-limiting list of target proteins is provided in Section 5.4, below.

In another aspect, provided herein are compositions, e.g., pharmaceutical compositions, comprising the glycosylated (e.g., sialylated/polysialylated) target proteins produced by the host cells provided herein. See Section 5.5, below.

In a specific embodiment, provided herein is a composition comprising glycosylated proteins produced using a host cell described herein, wherein at least 80%, 85%, 90%, 95%, or 99% of the N-glycosylation consensus sequences present in said proteins comprise a glucose linked to the Asn residue (or other relevant residue) present in the N-glycosylation consensus sequence.

In another specific embodiment, provided herein is a composition comprising glycosylated proteins produced using a host cell described herein, wherein at least 80%, 85%, 90%, 95%, or 99% of the N-glycosylation consensus sequences present in said proteins comprise an identical attached polysaccharide linked to the Asn residue (or other relevant residue) present in said N-glycosylation consensus sequences.

In another specific embodiment, provided herein is a composition comprising glycosylated proteins produced using a host cell described herein, wherein at least 80%, 85%, 90%, 95%, or 99% of the proteins in said composition have been N-glycosylated by the NGT of said host cell, e.g., an NGT encoded by a heterologous nucleic acid present in said host cell. In a specific embodiment, at least 80%, 85%, 90%, 95%, or 99% of the N-glycosylation consensus sequences present in each protein present in said composition comprise a glucose linked to the Asn residue present (or other relevant residue) in said N-glycosylation consensus sequences. In another specific embodiment, at least 80%, 85%, 90%, 95%, or 99% of the N-glycosylation consensus sequences present in each protein present in said composition comprise an identical attached polysaccharide linked to the Asn residue (or other relevant residue) present in said N-glycosylation consensus sequences.

In another specific embodiment, provided herein is a composition comprising sialylated proteins produced using a host cell described herein. In a specific embodiment, at least 80%, 85%, 90%, 95%, 96%, 97%, 98%, or 99% of said proteins in said composition are sialylated or polysialylated. In another specific embodiment, 100% of said proteins in said composition are sialylated or polysialylated. In another specific embodiment, at least 80%, 85%, 90%, 95%, or 99% of the N-glycosylation consensus sequences present in each protein present in said composition comprise an identical sialylation pattern at the Asn residue (or other relevant residue) present in said N-glycosylation consensus sequences.

In another aspect, provided herein are methods of treating a subject, e.g., a human subject, comprising administering to the subject an effective amount of a composition (e.g., pharmaceutical composition) described herein. See Section 5.6, below.

In another aspect, provided herein are kits comprising the host cells, proteins, and/or compositions provided herein.

3.1 Terminology

The term "about," when used in conjunction with a number, refers to any number within ±1, ±5 or ±10% of the referenced number.

As used herein, the term "N-glycosylation consensus sequence" refers to a sequence present in a target protein that an N-glycosyltransferase (NGT) is capable of adding a glucose to. In a specific embodiment, an N-glycosylation consensus sequence is Asparagine (Asn)-X-Serine (Ser)/Threonine (Thr), wherein X can be any amino acid except Proline (Pro). In another specific embodiment, an N-glycosylation consensus sequence is Y—X—Z, wherein Y can be Asparagine (Asn), Glutamine (Gln), or Serine (Ser), X can be any amino acid except Pro, and Z can be any amino acid. In a specific embodiment, Z is Ser, Thr, Glycine (Gly), Valine (Val), Alanine (Ala), or Aspartate (Asp).

As used herein, the term "effective amount," in the context of administering a therapy (e.g., a composition described herein) to a subject refers to the amount of a therapy which has a prophylactic and/or therapeutic effect(s). In certain embodiments, an "effective amount" refers to the amount of a therapy which is sufficient to achieve one, two, three, four, or more of the following effects: (i) reduce or ameliorate the severity of a disease/disorder or symptom associated therewith; (ii) reduce the duration of a disease/disorder or symptom associated therewith; (iii) prevent the progression of a disease/disorder or symptom associated therewith; (iv) cause regression of a disease/disorder or symptom associated therewith; (v) prevent the development or onset of a disease/disorder, or symptom associated therewith; (vi) prevent the recurrence of a disease/disorder or symptom associated therewith; (vii) reduce organ failure associated with a disease/disorder; (viii) reduce hospitalization of a subject having a disease/disorder; (ix) reduce hospitalization length of a subject having a disease/disorder; (x) increase the survival of a subject with a disease/disorder; (xi) eliminate a disease/disorder in a subject; and/or (xii) enhance or improve the prophylactic or therapeutic effect(s) of another therapy.

As used herein, the term "subject" refers to an animal (e.g., birds, reptiles, and mammals). In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet (e.g., a dog, cat, horse, goat, sheep, pig, donkey, or chicken). In a specific embodiment, a subject is a human. The terms "subject" and "patient" may be used herein interchangeably.

4. BRIEF DESCRIPTION OF THE DRAWINGS

FIG. 1: Metabolically engineered pathway for N-linked polysialylation of proteins in the bacterial cytoplasm. Initial site-specific modification of the target protein is achieved by the ApNGT, which adds a single N-linked glucose in the Asn-X-Ser(Thr) consensus sequon. Sequential elongation of the glucose is achieved by the galactosyltransferase (LgtB), sialyltransferase (CstII), and polysialyltransferase (polyST). The donor molecule CMP-Neu5Ac is either synthesized from an exogenous supply of Neu5Ac (scavenger pathway) or with an endogenous synthesis of Neu5Ac from UDP-GlcNAc (de novo pathway). Glycans are drawn in accordance with the guidelines of the Consortium for Functional Glycomics.

Figure 2:
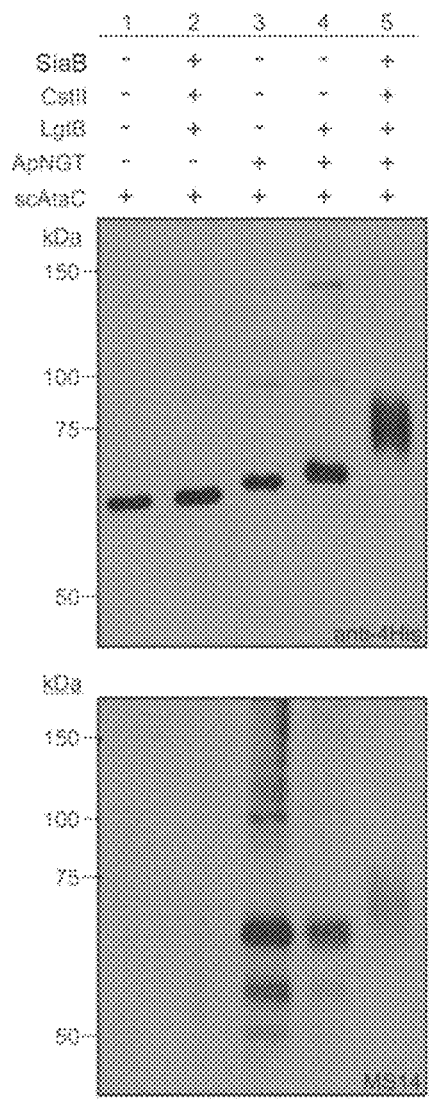

FIG. 2: Assembly of sialyllactose on scAtaC. The artificial glycosylation pathway was tested using scAtaC as target protein. The scAtaC construct is a cytoplasmically retained fragment (aa1866-2428) of an autotransporter and contains a total of 13 potential glycosylation sites and a 6×His tag. The scAtaC construct was co-expressed in E. coli JM107 ΔnanA:kan together with the full sialyllactose pathway (lane 5), or with truncated glycosylation pathways containing only the ApNGT construct (lane 3), or the ApNGT and LgtB constructs (lane 4). Control strains expressed either no glycosyltransferases (lane 1) or no ApNGT (lane 2). Protein expression was carried out for 20 hours at 28° C. and scAtaC was enriched using NiNTA beads in batch format. Eluted proteins were separated on SDS-PAGE, and scAtaC was detected via immunoblot against the 6×His tag (upper panel) or against N-linked glucose (lower panel).

Figure 3:
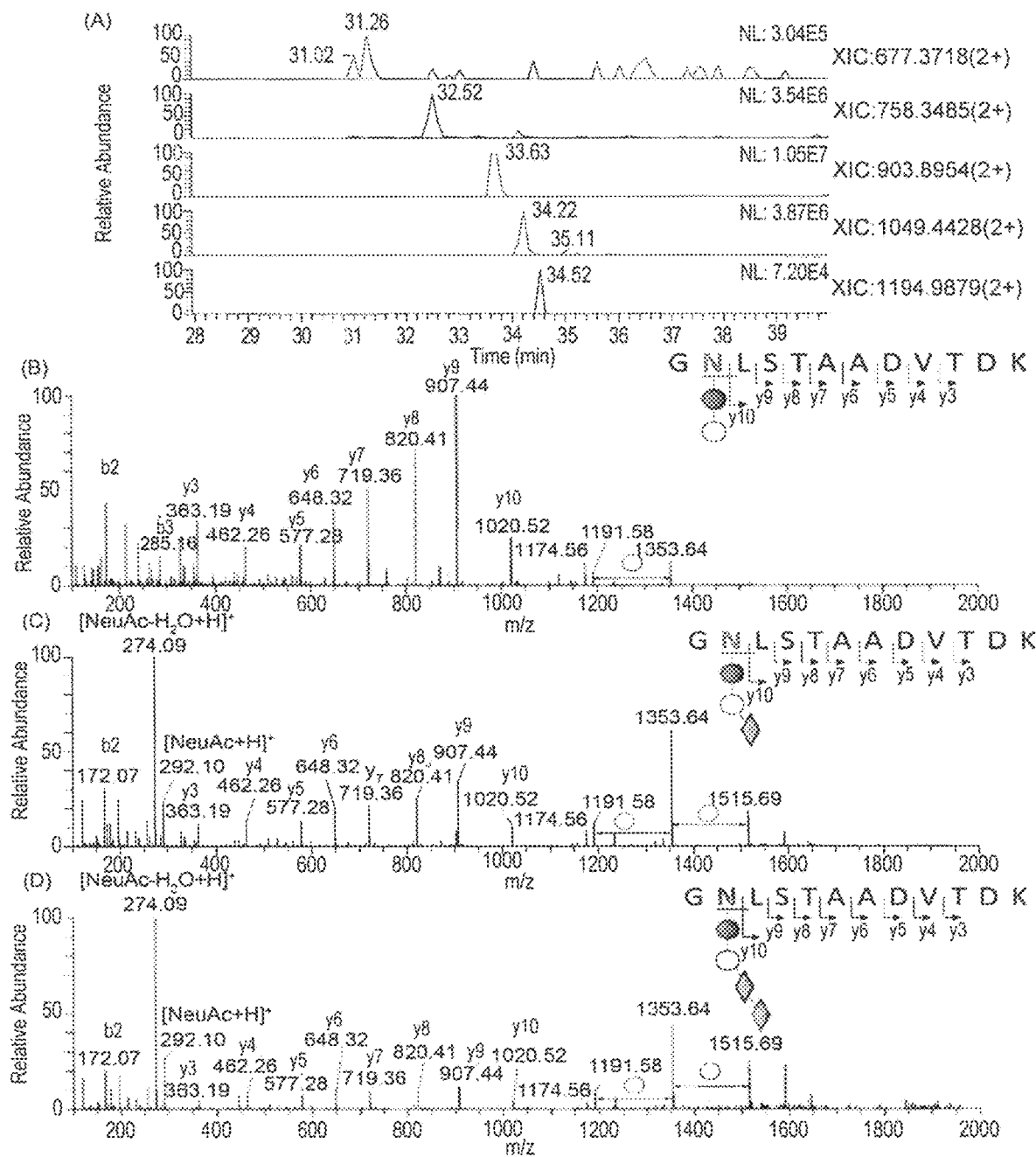

FIG. 3: Assembly of N-linked sialyllactose on scAtaC is confirmed by nanoLC-MS/MS. The scAtaC construct was co-expressed in *E. coli* JM107 ΔnanA:kan together with the full sialyllactose pathway then purified via NiNTA beads. The purified protein was subjected directly to tryptic digest and analyzed by nano-LC-MS/MS. (A) The extract ion chromatogram (XIC) of one tryptic peptide from scAtaC, G NLSTAADVTDK (N: potential N-glycosylation site; SEQ ID NO:4), with its corresponding glycoform is shown in each chromatogram. Addition of each sialic acid to the peptide increases the retention time on reverse phase chromatography. HCD MS/MS spectra of m/z 758.3485 (z=2) (B), 903.8954 (z=2) (C) and 1049.4428 (z=2) (D) revealed consecutive peptide fragment ions and glycan neutral loss. For sialylated glycopeptides, the oxonium ions of [NeuAc-H2O+H]$^+$ and [NeuAc+H]$^+$ were observed in (C) and (D). Sugar symbols follow the Consortium for Functional Glycomics guidelines.

Figure 4:
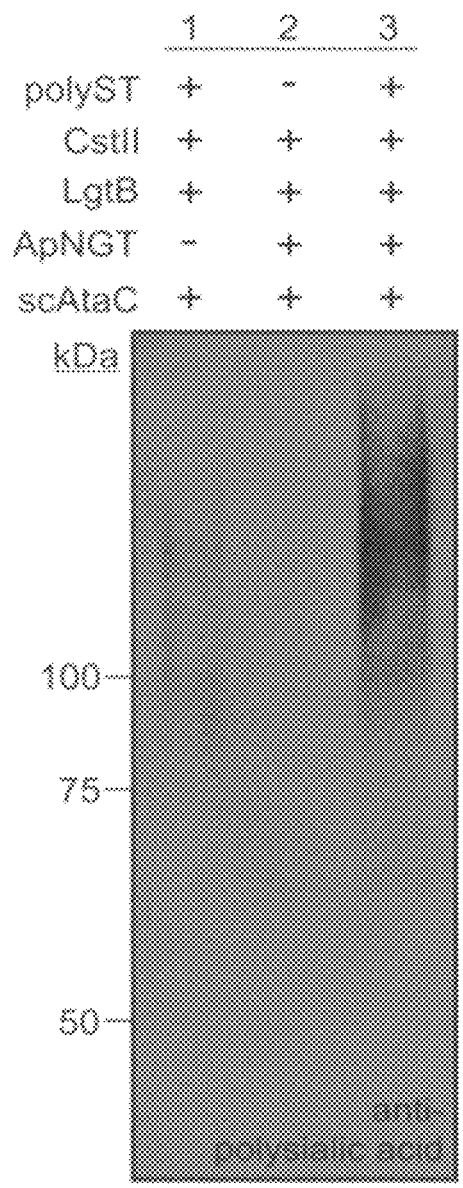

FIG. 4: Assembly of polysialic acid on scAtaC. The artificial glycosylation pathway was tested using scAtaC as target protein. The scAtaC construct was co-expressed in *E. coli* JM107 ΔnanA:kan together with the full polysialylation pathway (lane 3). Control strains expressed either no ApNGT (lane 1) or no polyST (lane 2). Protein expression was carried out for 20 hours at 28 degrees and scAtaC was enriched using NiNTA beads in batch format. Eluted proteins were separated on SDS-PAGE, and polysialic acid was detected via immunoblot using a polysialic acid specific monoclonal antibody.

Figure 5:
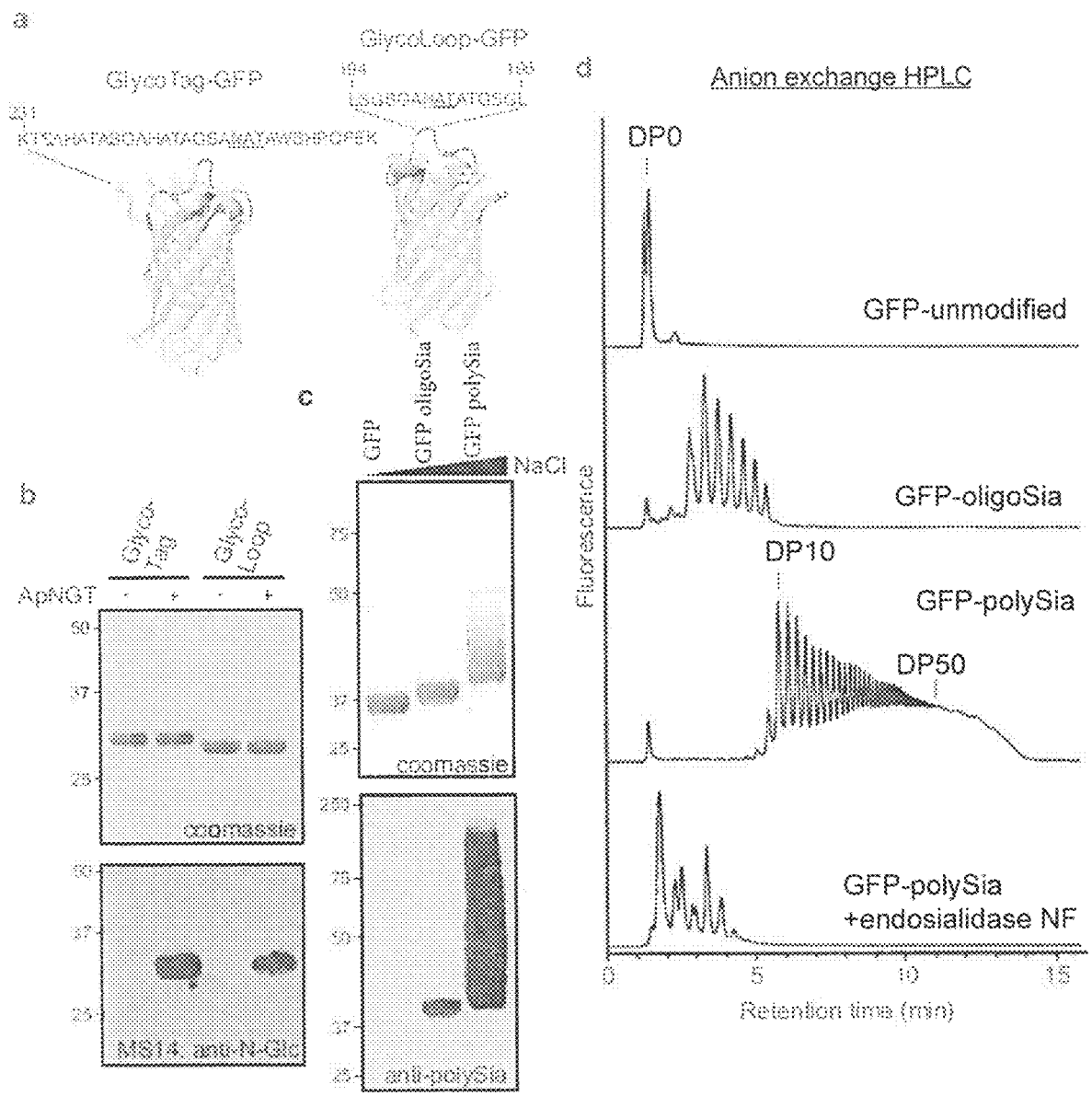

FIG. 5: Polysialylation of GFP. (a) Cartoon representation of the "GlycoTag-GFP" (SEQ ID NO:5) and "GlycoLoop-GFP" (SEQ ID NO:6). Each construct contains a single Asn-Ala-Thr glycosylation sequon (underlined) in a C-terminal extension and a loop insertion, respectively. The target asparagine residue is is the underlined Asn in the underlined Asn-Ala-Thr glycosylation sequon. The GlycoTag-GFP additionally comprises a C-terminal Strep-tag downstream of the underlined glycosylation sequon. (b) Gel and immunoblot analysis of purified GlycoTag- and GlycoLoop-GFP constructs, with and without glucosylation. Each GFP construct was expressed for 20 hours at 28° C. in the presence or absence of the ApNGT. The GFPs were double affinity purified via NiNTA and Streptactin Sepharose beads. Purified proteins were separated by SDS-PAGE and either Coomassie stained (upper panel) or analyzed by immunoblot (lower panel) to detect N-linked glucose using the human serum MS1413. (c) Gel and immunoblot analysis of fractions from the purification of polysialylated GlycoTag-GFP. The protein was coexpressed with the full polysialylation pathway for 20 hours at 28° C. Total GFP was purified via NiNTA affinity chromatography, then fractionated via anion exchange chromatography into low, medium, and high [NaCl] elution fractions. The samples were exchanged into low salt buffer, separated by SDS-PAGE and either Coomassie stained (upper panel) or analyzed by immunoblot (lower panel) to detect polySia. (d) Determination of polymer length by UPLC analysis of intact glycoproteins. The purified oligo- and polysialylated GlycoTag-GFP were compared with unmodified protein (expressed in the absence of glycosylation machinery). Each sample was separated on a ProPac SAX column in a linear gradient from 50 to 600 mM NaCl in 20 mM Tris pH 7.0 at a flow rate of 1.2 ml/min over 15 minutes. Elution of GFP glycoforms was monitored by on-line fluorescence detection (Ex. 385/Em. 410). The degree of polymerisation (DP) is indicated for selected peaks. The chemical identity of a2,8-linked polySia acid on GFP was confirmed by digestion of the polysaccharide with a specific depolymerase, endosialidase NF.

Figure 6:
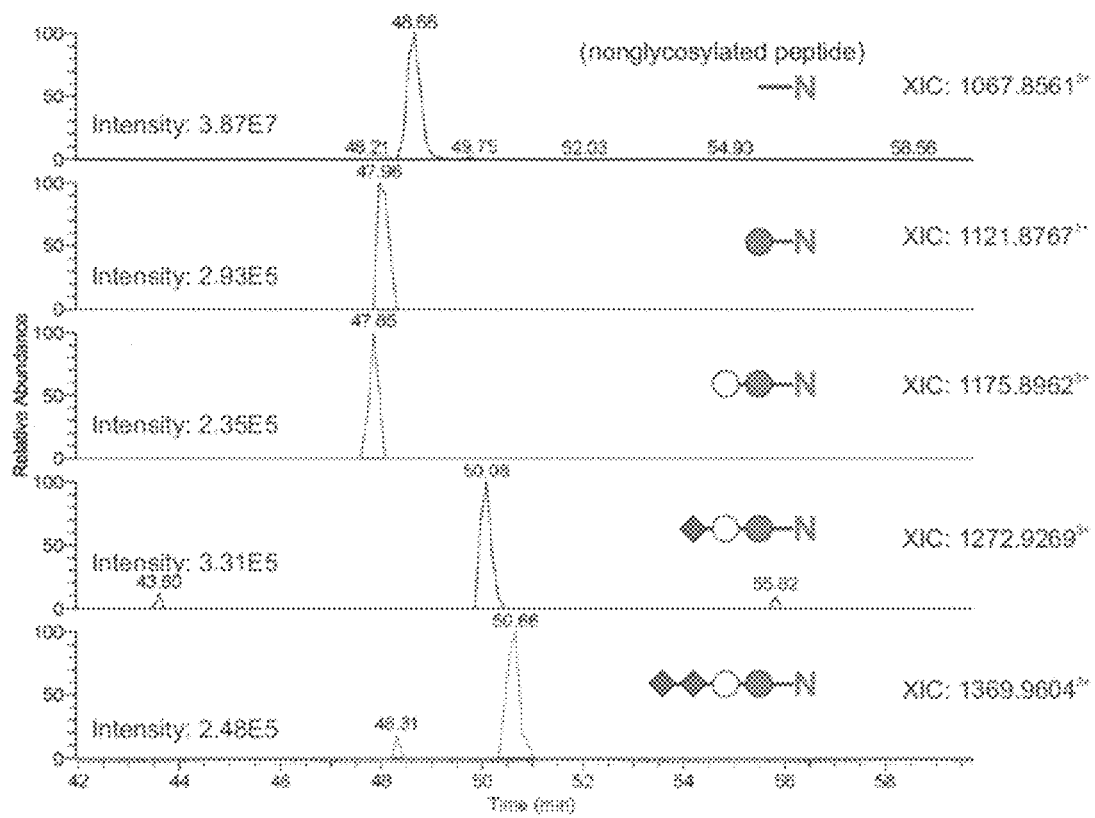

FIG. 6: NanoLC-MS/MS demonstrates assembly of N-linked sialyllactose on GlycoLoop-GFP. The GlycoLoop-GFP construct was co-expressed in *E. coli* JM107 ΔnanA:kan together with the sialyllactose pathway, then enriched via NiNTA beads. The enriched protein was subjected directly to tryptic digest and nano-LC-MS/MS analysis. The peptide sequence (top) and extract ion chromatograms (XIC) of the glycosite containing tryptic peptide (SEQ ID NO:7) from GlycoLoop-GFP, with its corresponding glycoform is shown in each chromatogram. Sugar symbols follow the Consortium for Functional Glycomics guidelines.

Figure 7:
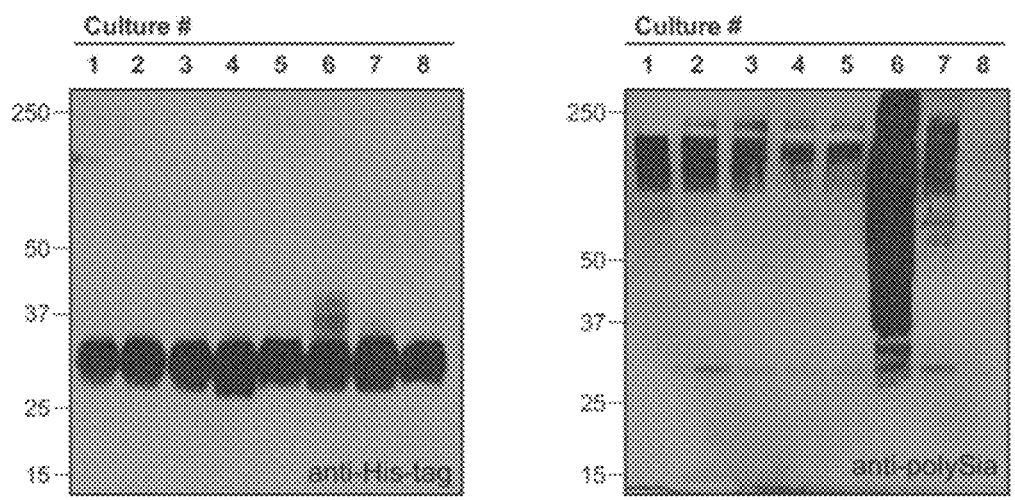

FIG. 7: Optimization of shaker flask culture conditions for polysialylation of GlycoTag-GFP. The *E. coli* JM107 ΔnanA:kan strain carrying expression plasmids for the polysialylation pathway and the GlycoTag-GFP were cultivated and expressed in 100 ml flasks. Each culture was carried out with a variation on the standard expression conditions as outlined in (a). Whole cell extracts were separated by SDS-PAGE on 10% acrylamide gels and polysialylation of GFP was monitored by immunoblot analysis directed against the 10×His tag on GFP (left panel) or polySia (right panel) (b).

Figure 8:
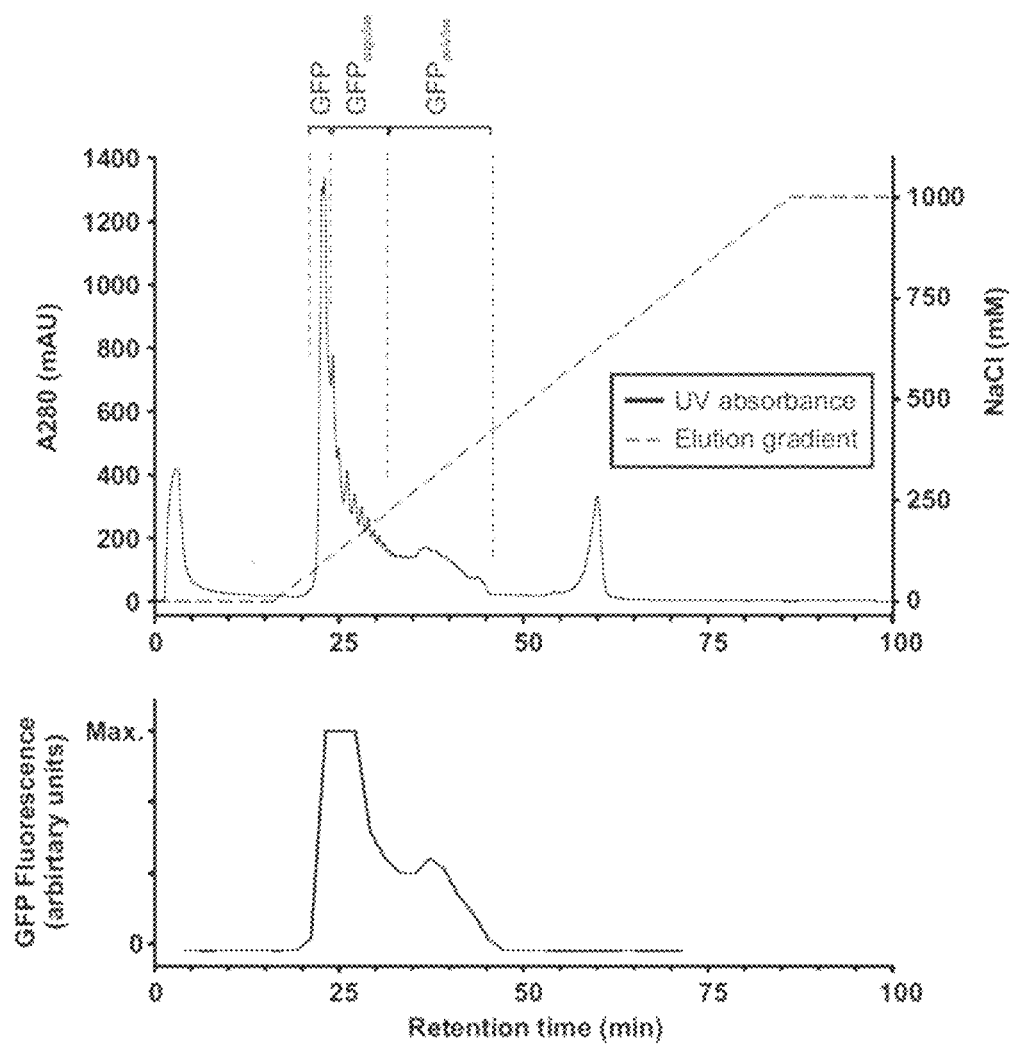

FIG. 8: Fractionation of GlycoTag-GFP glycoforms via preparative strong anion exchange chromatography. Total GFP was purified via NiNTA affinity chromatography. The concentrated eluate was loaded directly on a MonoQ strong anion exchange column and separated in a gradient from 0-1 M NaCl (top panel) in 20 mM Tris pH 7.0 at a flow rate of 1 ml/min. The GFP containing fractions were identified by visual inspection and confirmed by measuring fluorescence of each fraction (Ex. 485 nm/Em. 520 nm, bottom panel). The indicated fractions "GFP", "GFP$_{oligoSia}$", and "GFP$_{polySia}$" were collected, buffer exchanged, and retained for further analysis (see FIGS. 5c and d).

Figure 9:
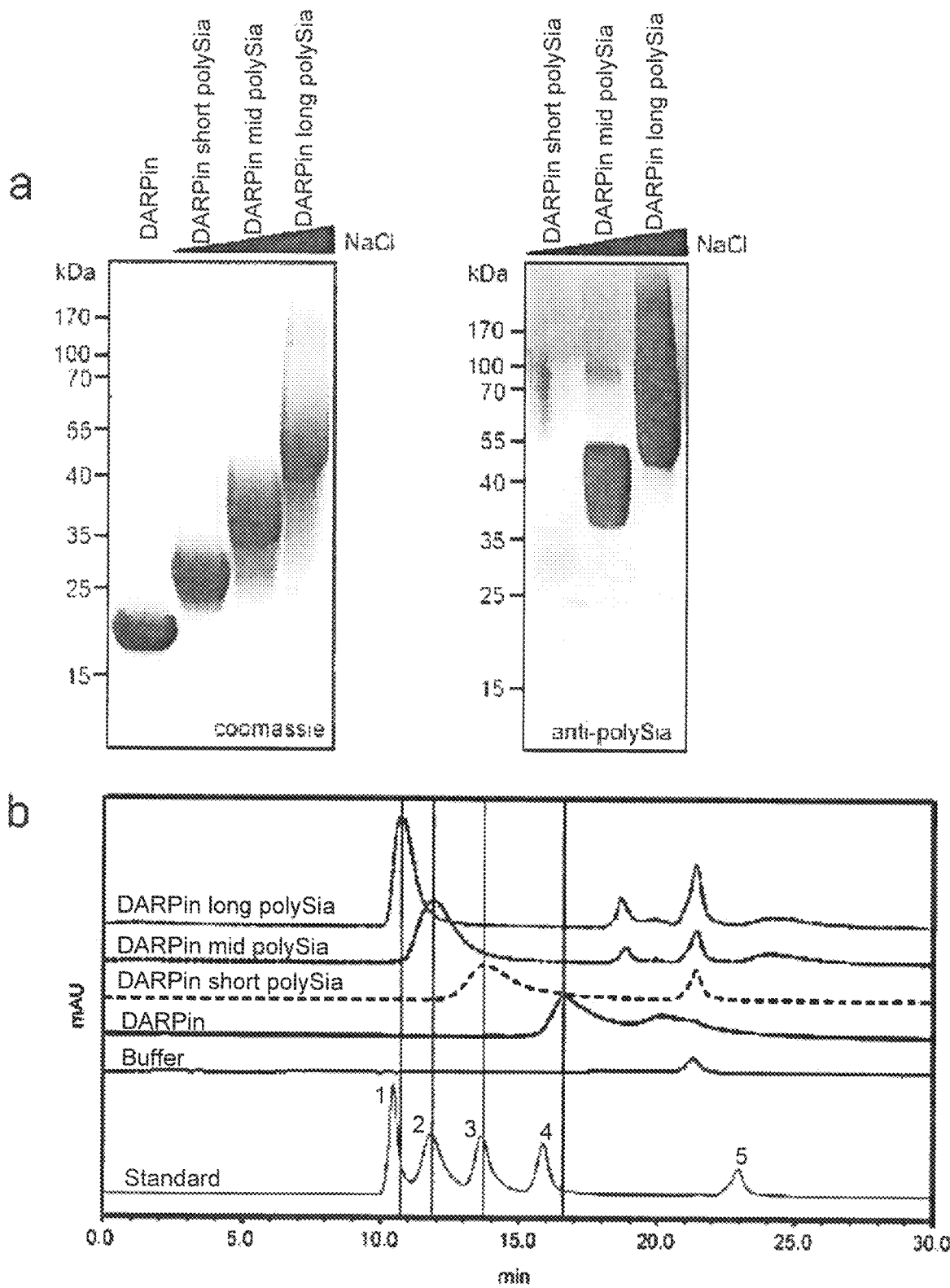

FIG. 9: Polysialylation of a VEGF-A-antagonistic DARPin. (a) Gel and immunoblot analysis of fractions from the purification of polysialylated GlycoTag-DARPin. The GlycoTag-DARPin protein was co-expressed with the full polysialylation pathway for 20 hours at 28° C. Total GlycoTag-DARPin was purified via NiNTA affinity chromatography, then fractionated via anion exchange chromatography into low, medium, and high NaCl concentration elution fractions. After the final size exclusion chromatography step, the samples were separated by SDS-PAGE and either stained by Coomassie (left panel) or analyzed by immunoblot (right panel) to detect polySia. (b) Analysis of purified proteins by HPSEC. The purified polysialylated GlycoTag-DARPin preparations (modified with short, mid and long polySia) were compared with unmodified protein (expressed in the absence of glycosylation machinery). Each sample was separated on an Agilent Bio SEC-5 column and absorbance at 215 nm was monitored online. The gel filtration standard contained following components: (1) Thyroglobulin (bovine) MW=670 kDa, (2) v-globulin (bovine) MW=158 kDa, (3) Ovalbumin (chicken) MW=44 kDa, (4) Myoglobin (horse) MW=17 kDa and (5) Vitamin B$_{12}$ MW=1.35 kDa.

Figure 10:
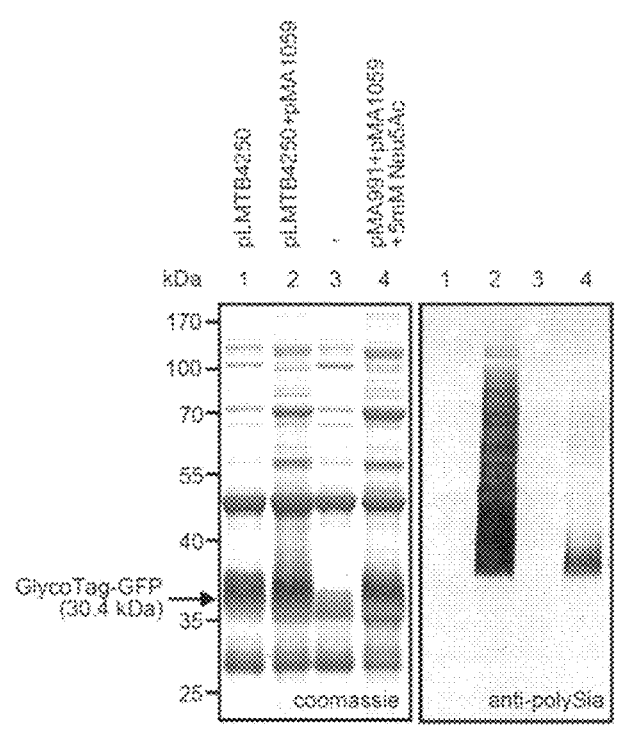

FIG. 10: Polysialylation of GFP using the de novo pathway for biosynthesis of CMP-Neu5Ac. GlycoTag-GFP was co-expressed in *E. coli* W3110 ΔlacZ ΔnanA ΔnanK together with the full polysialylation pathway encoding the genes for de novo synthesis of CMP-Neu5Ac, siaABC (lane 2). Control strains expressed the full polysialylation pathway with an exogenous supply of Neu5Ac (lane 4), no polyST (lane 1) or no glycosylation pathway (lane 3). Protein expression was carried out for 20 hours at 28° C., GFP was enriched using NiNTA beads in batch format. Eluted proteins were separated on SDS-PAGE and either stained by Coomassie (left panel) or analysed by immunoblot to detect polySia (right panel).

Figure 11:
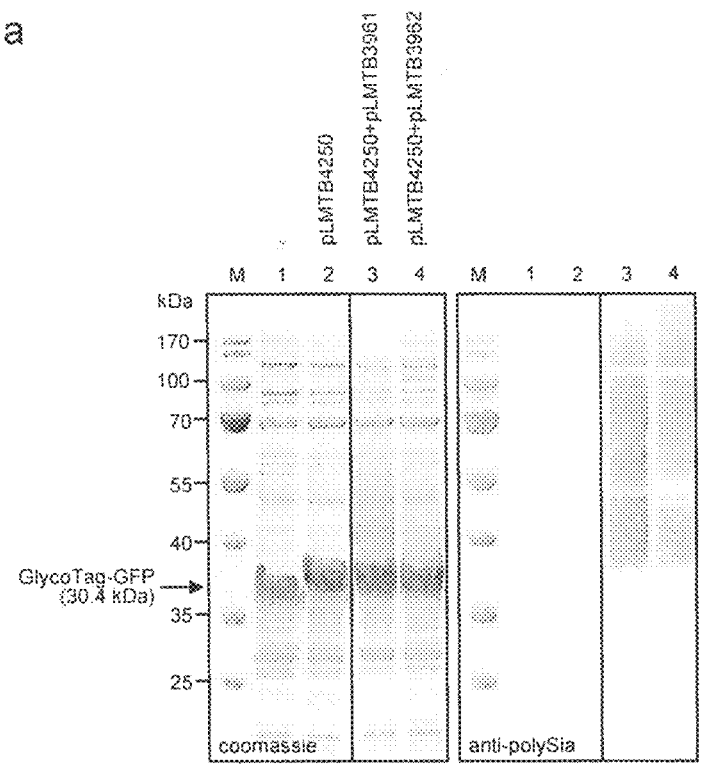
Figure 11:
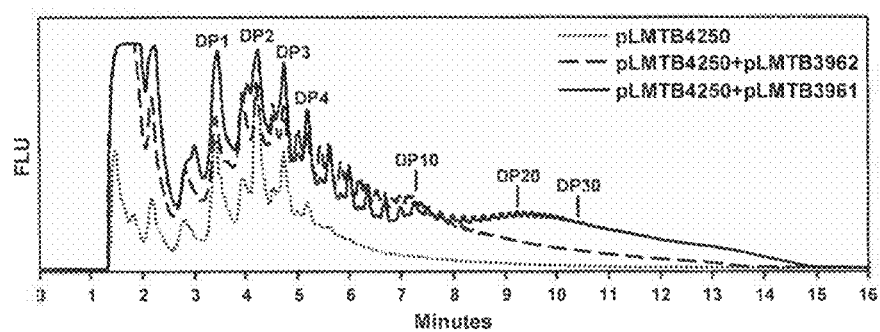

FIG. 11: Polysialylation of GFP using polyST homologs. GlycoTag-GFP was co-expressed in E. coli W3110 ΔlacZ ΔnanA ΔnanK together with the full polysialylation pathway encoding the genes for de novo synthesis of CMP-Neu5Ac, siaABC, and Δ20polyST$_{Mh}$ (lane 3) or the MalE-Δ20polyST$_{Mh}$ fusion variant (lane 4). Control strains expressed the full de novo sialyllactose pathway (lane 2), or no glycosylation pathway (lane 1). Protein expression was carried out for 20 hours at 28° C., GFP was enriched using NiNTA beads in batch format. (a) Gel and immunoblot analysis of enriched GlycoTag-GFP. The samples were separated by SDS-PAGE and either stained by Coomassie (left panel) or analyzed by immunoblot (right panel) to detect polySia. (b) Determination of polymer length by HPAE analysis of intact glycoproteins. The enriched GlycoTag-GFP samples were separated on a ProPac SAX column in a linear gradient from 50 to 600 mM NaCl in 20 mM Tris pH 7.0 at a flow rate of 1.2 ml/min over 16 minutes. Elution of GFP glycoforms was monitored by on-line fluorescence detection (Ex. 385/Em. 410). The degree of polymerisation (DP) is indicated for selected peaks.

5. DETAILED DESCRIPTION

N-glycosyltransferases (NGT) are capable of adding a glucose to an amino acid present in an N-glycosylation consensus sequence. For example, NGTs can N-glycosylate the asparagine (Asn) residue present in the N-glycosylation consensus sequence Asn-X-Ser(Thr), wherein X can be any amino acid except Pro. NGTs also can N-glycosylate other N-glycosylation consensus sequences. See Section 5.1. As disclosed herein, it has been discovered by the inventors that when a monosaccharide, e.g., galactose, is linked to the glucose added by the NGT, the resulting Asn-glucose-monosaccharide (e.g., galactose) can serve as a primer for synthesis of oligosaccharides/polysaccharides, resulting in the production of glycosylated proteins. This discovery allows for the glycosylation of proteins of choice, including peptides and polypeptides, collectively referred to herein as "target proteins," either in vivo or in vitro. In particular, various glycosyltransferases can be selected and combined with an NGT and a target protein that comprises one or more N-glycosylation consensus sequences, resulting in (i) glucosylation (addition of a glucose) to the asparagine (Asn) (or other relevant residue) in the consensus sequence; (ii) linkage of a monosaccharide (e.g., galactose) to the glucose; and (iii) assembly of an oligosaccharide or polysaccharide on the glucose-monosaccharide primer. Therefore, provided herein are methods of producing glycosylated target proteins, said methods comprising (i) using an NGT to add a glucose to a target protein that comprises one or more N-glycosylation consensus sequences; (ii) using a glycosyltransferase (e.g., a galactosyltransferase) to add a monosaccharide (e.g., galactose) to said glucose; and (iii) using one or more additional glycosyltransferases to generate an oligosaccharide or polysaccharide on the glucose-monosaccharide primer.

Host cells comprising machinery for the production of glycosylated target proteins are described in Section 5.1. Methods for introducing glycosylation machinery into the host cells described herein are provided in Section 5.2. Methods of producing glycosylated target proteins are provided in Section 5.3. Specific target proteins that can be incorporated into the host cells provided herein, and that thus can be glycosylated using the host cells and methods described herein are detailed in Section 5.4. Compositions are provided in Section 5.5. Methods of using the compositions provided herein, e.g., in the treatment of disease, are provided in Section 5.6.

5.1 Host Cells

In one aspect, provided herein are host cells capable of producing glycosylated proteins, e.g., N-glycosylated proteins. The host cells provided herein comprise, inter alia, (i) a nucleic acid that encodes an N-glycosyltransferase (NGT) that is capable of adding a glucose to the Asn residue (or other relevant residue) present in an N-glycosylation consensus sequence and (ii) a nucleic acid that encodes a glycosyltransferase that catalyzes addition of a monosaccharide, e.g., galactose, to the glucose added by the NGT. The host cells provided herein provide a novel system for protein glycosylation in vivo, wherein glycosylated proteins are produced in the cytoplasm of the host cells. Importantly, the host cells provided herein circumvent the need to produce glycosylated proteins in the periplasm, a limitation of currently existing in vivo glycosylation platforms.

In a specific embodiment, provided herein is a host cell comprising (i) a nucleic acid that encodes a target protein comprising an N-glycosylation consensus sequence; (ii) a nucleic acid that encodes an N-glycosyltransferase (NGT) that adds glucose to the Asn residue (or other relevant residue) present in said N-glycosylation consensus sequence, and (iii) a nucleic acid that encodes a glycosyltransferase that catalyzes addition of a monosaccharide to said glucose. In a specific embodiment, said target protein is heterologous to the host cell. In another specific embodiment, said NGT is heterologous to the host cell. In another specific embodiment, said glycosyltransferase that catalyzes addition of a monosaccharide to said glucose is heterologous to the host cell. In another specific embodiment, each of said target protein, said NGT and said glycosyltransferase that catalyzes addition of a monosaccharide to said glucose are heterologous to the host cell. In another specific embodiment, said host cell is E. coli.

In another specific embodiment, provided herein is a host cell comprising (i) a nucleic acid that encodes a target protein comprising an N-glycosylation consensus sequence; (ii) a nucleic acid that encodes an N-glycosyltransferase (NGT) that adds glucose to the Asn residue (or other relevant residue) present in said N-glycosylation consensus sequence, (iii) a nucleic acid that encodes a glycosyltransferase that catalyzes addition of a monosaccharide to said glucose; and (iv) a nucleic acid that encodes a sialyltransferase. In a specific embodiment, said sialyltransferase adds one or more sialic acid residues to said galactose. In another specific embodiment, said target protein is heterologous to the host cell. In another specific embodiment, said NGT is heterologous to the host cell. In another specific embodiment, said glycosyltransferase that catalyzes addition of a monosaccharide to said glucose is heterologous to the host cell. In another specific embodiment, said sialyltransferase is heterologous to the host cell. In another specific embodiment, each of said target protein, said NGT, said sialyltransferase, and said glycosyltransferase that catalyzes addition of a monosaccharide to said glucose are heterologous to the host cell. In another specific embodiment, said host cell is *E. coli*.

In another specific embodiment, provided herein is a host cell comprising (i) a nucleic acid that encodes a target protein comprising an N-glycosylation consensus sequence; (ii) a nucleic acid that encodes an N-glycosyltransferase (NGT) that adds glucose to the Asn residue present (or other relevant residue) in said N-glycosylation consensus sequence, (iii) a nucleic acid that encodes a glycosyltransferase that catalyzes addition of a monosaccharide to said glucose; (iv) a nucleic acid that encodes a sialyltransferase; and (v) a nucleic acid that encodes a polysialyltransferase (polyST). In a specific embodiment, said sialyltransferase adds one or more sialic acid residues to said galactose and said polyST synthesizes polysialic acid, allowing for production of polysialylated proteins with improved pharmacokinetic properties by said host cell. In another specific embodiment, said target protein is heterologous to the host cell. In another specific embodiment, said NGT is heterologous to the host cell. In another specific embodiment, said glycosyltransferase that catalyzes addition of a monosaccharide to said glucose is heterologous to the host cell. In another specific embodiment, said sialyltransferase is heterologous to the host cell. In another specific embodiment, said polyST is heterologous to the host cell. In another specific embodiment, each of said target protein, said NGT, said sialyltransferase, said polyST, and said glycosyltransferase that catalyzes addition of a monosaccharide to said glucose are heterologous to the host cell. In another specific embodiment, said host cell is *E. coli*.

In another specific embodiment, provided herein is a host cell comprising (i) a nucleic acid that encodes a target protein comprising an N-glycosylation consensus sequence; (ii) a nucleic acid that encodes an N-glycosyltransferase (NGT) that adds glucose to the Asn residue (or other relevant residue) present in said N-glycosylation consensus sequence, (iii) a nucleic acid that encodes a glycosyltransferase that catalyzes addition of a monosaccharide to said glucose; (iv) a nucleic acid that encodes a sialyltransferase; (v) a nucleic acid that encodes a polysialyltransferase (polyST); and (vi) a nucleic acid that encodes a CMP-Neu5Ac synthetase. In a specific embodiment, said sialyltransferase adds one or more sialic acid residues to said galactose and said polyST synthesizes polysialic acid, allowing for production of polysialylated proteins with improved pharmacokinetic properties by said host cell. In another specific embodiment, said target protein is heterologous to the host cell. In another specific embodiment, said NGT is heterologous to the host cell. In another specific embodiment, said glycosyltransferase that catalyzes addition of a monosaccharide to said glucose is heterologous to the host cell. In another specific embodiment, said sialyltransferase is heterologous to the host cell. In another specific embodiment, said polyST is heterologous to the host cell. In another specific embodiment, said CMP-Neu5Ac synthetase is heterologous to the host cell. In another specific embodiment, each of said target protein, said NGT, said sialyltransferase, said polyST, said CMP-Neu5Ac synthetase, and said glycosyltransferase that catalyzes addition of a monosaccharide to said glucose are heterologous to the host cell. In another specific embodiment, said host cell is *E. coli*.

In a specific embodiment, the host cells provided herein comprise a nucleic acid that encodes the NGT of a species of *Actinobacillus*. In a specific embodiment, said NGT is the NGT of *Actinobacillus pleuropneumoniae* (SEQ ID NO:1). See, e.g., Choi et al., PLoS ONE (2010). In another specific embodiment, said NGT is the NGT of *Actinobacillus suis*, *Actinobacillus succinogenes*, *Actinobacillus minor*, or *Actinobacillus capsulatus*.

In another specific embodiment, the host cells provided herein comprise a nucleic acid that encodes the NGT of a species of *Haemophilus*, e.g., *Haemophilus aegyptius*, *Haemophilus ducreyi*, *Haemophilus haemolyticus*, *Haemophilus influenza*, *Haemophilus parainfluenzae*, *Haemophilus parahaemolyticus*, *Haemophilus pittmaniae*, or *Haemophilus sputorum*.

In another specific embodiment, the host cells provided herein comprise a nucleic acid that encodes the NGT of a species of *Mannheimia*, e.g., *Mannheimia granulomatis*, *Mannheimia haemolytica*, *Mannheimia succiniproducens*, or *Mannheimia varigena*.

In another specific embodiment, the host cells provided herein comprise a nucleic acid that encodes the NGT of a species of *Bibersteinia*, e.g., *Bibersteinia trehalosi*.

In another specific embodiment, the host cells provided herein comprise a nucleic acid that encodes the NGT of a species of *Yersinia*, e.g., *Yersinia bercovieri*, *Yersinia enterocolitica*, *Yersinia frederiksenii*, *Yersinia intermedia*, *Yersinia kristensii*, *Yersinia mollaretii*, *Yersinia pestis*, *Yersinia pseudotuberculosis*, *Yersinia rhodei*, or *Yersinia similis*.

In certain embodiments, the NGT used in the host cells provided herein is one that is homologous to the NGT of any one of *Actinobacillus* (e.g., the NGT of *Actinobacillus pleuropneumoniae*), *Haemophilus*, *Mannheimia*, *Bibersteinia*, or *Yersinia*. For example, a host cell provided herein may comprise a nucleic acid that is about 70%, 75%, 80%, 85%, 90%, 95%, 96%, 97%, 98%, or 99% homologous to the nucleic acid that encodes an NGT of *Actinobacillus* (e.g., the NGT of *Actinobacillus pleuropneumoniae*), *Haemophilus*, *Mannheimia*, *Bibersteinia*, or *Yersinia*.

In certain embodiments, the nucleic acid that encodes a glycosyltransferase that catalyzes addition of a monosaccharide to said glucose present in the host cells provided herein encodes a galactosyltransferase. In a specific embodiment, said galactosyltransferase is the LgtB of a species of *Neisseria*. In a specific embodiment, said galactosyltransferase is LgtB of *N. meningitidis*. In another specific embodiment, said galactosyltransferase is LgtB of *N. gonorrhoeae*. In another specific embodiment, said galactosyltransferase is LgtE of *N. meningitidis*. In another specific embodiment, said galactosyltransferase is CgtB of *C. jejuni*. In another specific embodiment, said galactosyltransferase is WaaX of *E. coli*. In another specific embodiment, said galactosyltransferase is HP0826 of *Helicobacter pylori*. In another specific embodiment, said galactosyltransferase is a eukaryotic β4Gal-T1.

In certain embodiments, the galactosyltransferase used in the host cells provided herein is one that is homologous to a galactosyltransferase of *Neisseria*, *Campylobacter*, *E. coli*, *Helicobacter pylori*, or a eukaryotic galactosyltransferase. For example, a host cell provided herein may comprise a nucleic acid that is about 70%, 75%, 80%, 85%, 90%, 95%, 96%, 97%, 98%, or 99% homologous to a nucleic acid that encodes an LgtB of a species of *Neisseria* (e.g., LgtB of *N. meningitidis*, LgtB of *N. gonorrhoeae*, or LgtE of *N. meningitidis*); about 70%, 75%, 80%, 85%, 90%, 95%, 96%, 97%, 98%, or 99% homologous to the nucleic acid that encodes CgtB of *C. jejuni*; about 70%, 75%, 80%, 85%, 90%, 95%, 96%, 97%, 98%, or 99% homologous to the nucleic acid that encodes WaaX of *E. coli*; about 70%, 75%, 80%, 85%, 90%, 95%, 96%, 97%, 98%, or 99% homologous to the nucleic acid that encodes HP0826 of *Helicobacter*

*pylori*; or about 70%, 75%, 80%, 85%, 90%, 95%, 96%, 97%, 98%, or 99% homologous to the nucleic acid that encodes eukaryotic β4Gal-T1.

In another specific embodiment, when the host cells provided herein comprise a nucleic acid that encodes a sialyltransferase, said sialyltransferase from a species of *Campylobacter*. In a specific embodiment, said sialyltransferase is CstII of *C. jejuni*. In another specific embodiment, said sialyltransferase is CstI of *C. jejuni*. In another specific embodiment, said sialyltransferase is Lst of *N. meningitidis*. In another specific embodiment, said sialyltransferase is Lst of *N. gonorrhoeae*.

In certain embodiments, the sialyltransferase used in the host cells provided herein is one that is homologous to a sialyltransferase of *Neisseria* or *Campylobacter*. For example, a host cell provided herein may comprise a nucleic acid that is about 70%, 75%, 80%, 85%, 90%, 95%, 96%, 97%, 98%, or 99% homologous to the nucleic acid that encodes CstII of *C. jejuni*, CstI of *C. jejuni*, Lst of *N. meningitidis*, or Lst of *N. gonorrhoeae*.

In another specific embodiment, when the host cells provided herein comprise a nucleic acid that encodes a polysialyltransferase (polyST), said polyST is a polyST of *N. meningitidis*. In a specific embodiment, said polyST of *N. meningitidis* is a polyST of *N. meningitidis* serogroup B.

In another specific embodiment, when the host cells provided herein comprise a nucleic acid that encodes a polysialyltransferase (polyST), said polyST is a polyST of *E. coli* K1, *Mannheimania haemolytica*, or *Moraxella nonliquifacien*.

In certain embodiments, the polysialyltransferase used in the host cells provided herein is one that is homologous to a polysialyltransferase of a species of *Neisseria*, a species of *Mannheimania*, a species of *Moraxella*, or *E. coli*. For example, a host cell provided herein may comprise a nucleic acid that is about 70%, 75%, 80%, 85%, 90%, 95%, 96%, 97%, 98%, or 99% homologous to the nucleic acid that encodes the polyST of *N. meningitidis* serogroup B, the polyST of *Mannheimania haemolytica*, the polyST of *Moraxella nonliquifacien*, or the polyST of *E. coli*.

In another specific embodiment, when the host cells provided herein comprise a nucleic acid that encodes a CMP-Neu5Ac synthetase, said CMP-Neu5Ac synthetase is SynB of *N. meningitidis*.

In certain embodiments, the CMP-Neu5Ac synthetase used in the host cells provided herein is one that is homologous to a CMP-Neu5Ac synthetase of a species of *Neisseria*. For example, a host cell provided herein may comprise a nucleic acid that is about 70%, 75%, 80%, 85%, 90%, 95%, 96%, 97%, 98%, or 99% homologous to the nucleic acid that encodes SynB of *N. meningitidis*.

In certain embodiments, the host cells provided herein are prokaryotic host cells. Exemplary prokaryotic host cells include, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell used herein is *E. coli*.

In certain embodiments, the host cells provided herein are eukaryotic host cells. Exemplary eukaryotic host cells include, without limitation, yeast cells, plant cells, insect cells, kinetoplastida cells, and mammalian cells.

In certain embodiments, the nucleic acid that encodes a target protein present in the host cells provided herein encodes a therapeutic protein, i.e., a protein used in the treatment of a disease or disorder. For example, the nucleic acid that encodes a target protein present in the host cells provided herein can encode an enzyme, a cytokine, a receptor, a ligand, a growth factor, a protein that acts as an inhibitor, or an antibody. A non-limiting list of target proteins is provided in Section 5.4, below.

A nucleic acid encoding any protein known in the art can be incorporated into the host cells described herein. Accordingly, the host cells provided herein can be utilized to produce glycosylated (including sialylated and polysialylated) versions of any protein known in the art. In a specific embodiment, the host cells provided herein are used to produce sialylated versions of a protein. In another specific embodiment, the host cells provided herein are used to produce polysialylated versions of a protein. Exemplary proteins that can be produced using the host cells described herein are provided in Section 5.4. The host cells provided herein can be engineered to comprise a nucleic acid that encodes any of the proteins described in Section 5.4, and are thus capable of expressing such proteins.

In certain embodiments, the target proteins present in the host cells provided herein are expressed from a nucleic acid that has been introduced into the host cells using a plasmid, i.e., the plasmid contains a gene that encodes the particular target protein of interest.

In certain embodiments, the target proteins present in the host cells provided herein are expressed from a nucleic acid that has been integrated into the genome of the modified host cell. That is, a nucleic acid encoding the target protein has been integrated into the host cell genome.

In certain embodiments, the nucleic acid encoding a target protein present in a host cell provided herein has modified to include 1, 2, 3, 4, 5, 6, 7, 8, 9, 10, or more glycosylation sites (N-glycosylation consensus sequences) than would normally be associated with the target protein (e.g., relative to the number of glycosylation sites associated with the target protein in its native/natural, e.g., "wild-type" state).

In specific embodiments, introduction of glycosylation sites is accomplished by insertion of N-glycosylation consensus sequences (e.g., Asn-X-Ser(Thr), wherein X can be any amino acid except Pro) anywhere in the primary structure of the protein. In some embodiments, the consensus sequence is embedded in a heterologous sequence such that a heterologous sequence that comprises the N-glycosylation consensus sequence is embedded in the target protein, wherein said heterologous sequence is defined as an embedded glycosylation tag. Introduction of glycosylation sites can be accomplished by, e.g., adding new amino acids to the primary structure of the protein (i.e., the glycosylation sites are added, in full or in part), or by mutating existing amino acids in the protein in order to generate the glycosylation sites (i.e., amino acids are not added to the protein, but selected amino acids of the protein are mutated so as to form glycosylation sites). Those of skill in the art will recognize that the amino acid sequence of a protein can be readily modified using approaches known in the art, e.g., recombinant approaches that include modification of the nucleic acid sequence encoding the protein. In specific embodiments, N-glycosylation consensus sequences are introduced into specific regions of the target protein, e.g., surface structures of the protein, at the N or C termini of the protein, and/or in loops that are stabilized by disulfide bridges at the base of the protein. In certain embodiments, the said embedded glycosylation tag is at the surface of the otherwise folded target protein. In certain embodiments, the said embedded glycosylation tag is not part of the three-dimensional conformation of the target protein but remains unfolded. So that, without being bound by theory, the N-glycosylation consensus sequence remains more accessible to the N-glycosyltransferase.

In specific embodiments, introduction of glycosylation sites is accomplished by addition of an N-glycosylation consensus sequence (e.g., Asn-X-Ser(Thr), wherein X can be any amino acid except Pro) to the N or C terminus or both, the N and the C terminus, of a protein. In some embodiments, the consensus sequence is embedded in a heterologous sequence such that a heterologous sequence that comprises the N-glycosylation consensus sequence is added to the target protein, wherein said heterologous sequence attached to an N or C terminus is defined as a terminal glycosylation tag. In certain embodiments, said terminal glycosylation tag is at the surface of the otherwise folded target protein. In certain embodiments, the terminal glycosylation tag is not part of the three-dimensional conformation of the target protein but remains unfolded. So that, without being bound by theory, the N-glycosylation consensus sequence remains more accessible to the N-glycosyltransferase.

In another specific embodiment, the nucleic acid encoding a target protein comprises embedded glycosylation tags or terminal glycosylation tags. In another specific embodiment, the nucleic acid encoding a target protein comprises both embedded glycosylation tags and terminal glycosylation tags.

In certain embodiments, the target proteins produced using the host cells described herein comprise a "tag," i.e., a sequence of amino acids that allows for the isolation and/or identification of the target protein after its production by a host cell described herein. For example, adding a tag to a target protein described herein can be useful in the purification of that protein. Exemplary tags that can be used herein include, without limitation, histidine (HIS) tags (e.g., hexa histidine-tag, or 6×His-Tag), FLAG-TAG, and HA tags. In certain embodiments, a tag additionally comprises an embedded or terminal glycosylation tag as described herein. In certain embodiments, the tags used herein are removable, e.g., removal by chemical agents or by enzymatic means, once they are no longer needed, e.g., after the protein has been purified.

Glycosylation Machinery
N-Glycosyltransferases

N-glycosyltransferases (NGT) are capable of adding a glucose to an amino acid present in an N-glycosylation consensus sequence. For example, NGTs can N-glycosylate the asparagine (Asn) residue present in the N-glycosylation consensus sequence Asn-X-Ser(Thr), wherein X can be any amino acid except Pro. NGTs also can N-glycosylate the asparagine (Asn) residue present in the N-glycosylation consensus sequence Asn-X-Ala(Asp, Gly, or Val), wherein X can be any amino acid except Pro. NGTs also can N-glycosylate the Serine (Ser) residue present in the N-glycosylation consensus sequence Ser-X-Ser(Thr), wherein X can be any amino acid except Pro and the Glutamine (Gln) residue in the N-glycosylation consensus sequence Gln-X-Ser(Thr), wherein X can be any amino acid except Pro. In general, wild-type NGTs have a relaxed peptide substrate specificity and a relaxed donor substrate specificity: they can use UDP-Glc as well as UDP-Gal, UDP-Xyl, GDP-Glc and GDP-Man (see Naegeli et al., 2014, The Journal Of Biological Chemistry 289(35): 24521-24532).

Any NGT, or nucleic acid encoding it, capable of adding glucose to the Asn residue (or other relevant residue) in an N-glycosylation consensus sequence can be used in accordance with the methods described herein, e.g., can be incorporated in a host cell described herein.

In a specific embodiment, the host cells provided herein comprise a nucleic acid that encodes the NGT of a species of *Actinobacillus*. In a specific embodiment, said NGT is the NGT of *Actinobacillus pleuropneumoniae* (SEQ ID NO:1). See, e.g., Choi et al., PLoS ONE (2010). In another specific embodiment, said NGT is the NGT of *Actinobacillus suis*, *Actinobacillus succinogenes*, *Actinobacillus minor*, or *Actinobacillus capsulatus*.

In another specific embodiment, the host cells provided herein comprise a nucleic acid that encodes the NGT of a species of *Haemophilus*, e.g., *Haemophilus aegyptius*, *Haemophilus ducreyi*, *Haemophilus haemolyticus*, *Haemophilus influenza*, *Haemophilus parainfluenzae*, *Haemophilus parahaemolyticus*, *Haemophilus pittmaniae*, or *Haemophilus sputorum*.

In another specific embodiment, the host cells provided herein comprise a nucleic acid that encodes the NGT of a species of *Mannheimia*, e.g., *Mannheimia granulomatis*, *Mannheimia haemolytica*, *Mannheimia succiniproducens*, or *Mannheimia varigena*.

In another specific embodiment, the host cells provided herein comprise a nucleic acid that encodes the NGT of a species of *Bibersteinia*, e.g., *Bibersteinia trehalosi*.

In another specific embodiment, the host cells provided herein comprise a nucleic acid that encodes the NGT of a species of *Yersinia*, e.g., *Yersinia bercovieri*, *Yersinia enterocolitica*, *Yersinia frederiksenii*, *Yersinia intermedia*, *Yersinia kristensii*, *Yersinia mollaretii*, *Yersinia pestis*, *Yersinia pseudotuberculosis*, *Yersinia rhodei*, or *Yersinia similis*.

In certain embodiments, the NGT used in accordance with the methods described herein, e.g., incorporated in a host cell described herein, is one that is homologous to the NGT of any one of *Actinobacillus* (e.g., the NGT of *Actinobacillus pleuropneumoniae*), *Haemophilus*, *Mannheimia*, *Bibersteinia*, or *Yersinia*. For example, the NGT, or a nucleic acid encoding it, can be about 70%, 75%, 80%, 85%, 90%, 95%, 96%, 97%, 98%, or 99% homologous to the NGT of *Actinobacillus* (e.g., the NGT of *Actinobacillus pleuropneumoniae*), *Haemophilus*, *Mannheimia*, *Bibersteinia*, or *Yersinia*.

In other embodiments. The host cells provided herein comprise a nucleic acid that encodes the NGT of a species of *Aggregatibacter*, e.g., *Aggregatibacter aphrophilus*; *Bradyrhizobium*; *Burkholderia*, e.g., *Burkholderia bryophila*, *Burkholderia caledonica*, *Burkholderia caribensis*, *Burkholderia dilworthii*, *Burkholderia fungorum*, *Burkholderia graminis*, *Burkholderia grimmiae*, *Burkholderia phenoliruptrix*, *Burkholderia phymatum*, *Burkholderia phytofirmans*, *Burkholderia terrae*, and *Burkholderia xenovorans*; *Conchiformibius*, e.g., *Conchiformibius steedae*; *Cupriavidus*, e.g., *Cupriavidus metallidurans*; *Edwardsiella*, e.g., *Edwardsiella hoshinae*; Enterobacteriaceae; *Glaciecola*, e.g., *Glaciecola arctica*; *Gloeobacter*, e.g., *Gloeobacter kilaueensis*; *Herbaspirillum*, e.g., *Herbaspirillum frisingense*, *Herbaspirillum lusitanum*, *Herbaspirillum rubrisubalbicans*, or *Herbaspirillum seropedicae*; *Kingella*, e.g., *Kingella kingae*; *Kordiimonas*, e.g., *Kordiimonas gwangyangensis*; *Leptolyngbya*; *Limnobacter*; *Neisseria*, e.g., *Neisseria flavescens*; *Pasteurella*, e.g., *Pasteurella dagmatis* or *Pasteurella pneumotropica*; *Phenylobacterium*, e.g., *Phenylobacterium zucineum*; *Polaromonas*; *Providencia*, e.g., *Providencia rettgeri*; *Pseudanabaena*, e.g., *Pseudanabaena biceps*; *Pseudomonas*, e.g., *Pseudomonas agarici*, *Pseudomonas mendocina*, *Pseudomonas pseudoalcaligenes*, or *Pseudomonas tolaasii; Rheinheimera; Salmonella*, e.g., *Salmonella enterica*; or *Sulfurimonas*, or a homlog thereof.

Glycosyltransferase that Adds a Monosaccharide to Glucose

In certain embodiments, the methods provided herein utilize a glycosyltransferase that catalyzes addition of a monosaccharide to the glucose residue added by the NGT to the ASN residue (or other relevant residue) in the N-glycosylation consensus sequences of a target protein, e.g., the host cells provided herein can comprise a nucleic acid that encodes a glycosyltransferase that catalyzes addition of a monosaccharide to the glucose residue added by the NGT to the ASN residue (or other relevant residue) in the N-glycosylation consensus sequences of a target protein. Any glycosyltransferase, or nucleic acid encoding it, capable of adding a monosaccharide to said glucose can be used in accordance with the methods described herein.

In certain embodiments, the monosaccharide adding glycosyltransferase adds a lactose via a beta-1,4-linkage, resulting in a lactose-protein conjugate. In certain embodiments, the monosaccharide adding glycosyltransferase adds a lactose via a beta-1,3-linkage.

In a specific embodiment, the monosaccharide adding glycosyltransferase is a galactosyltransferase. Any galactosyltransferase, or nucleic acid encoding it, capable of adding galactose to said glucose can be used in accordance with the methods described herein.

In a specific embodiment, said galactosyltransferase is the LgtB of a species of *Neisseria*. In a specific embodiment, said galactosyltransferase is LgtB of *N. meningitidis*. In another specific embodiment, said galactosyltransferase is LgtB of *N. gonorrhoeae*. In another specific embodiment, said galactosyltransferase is LgtE of *N. meningitidis*. In another specific embodiment, said galactosyltransferase is CgtB of *C. jejuni*. In another specific embodiment, said galactosyltransferase is WaaX of *E. coli*. In another specific embodiment, said galactosyltransferase is HP0826 of *Helicobacter pylori*. In another specific embodiment, said galactosyltransferase is a eukaryotic β4Gal-T1.

In certain embodiments, the galactosyltransferase is one that is homologous to a galactosyltransferase of *Neisseria, Campylobacter, E. coli, Helicobacter pylori*, or a eukaryotic galactosyltransferase. For example, the galactosyltransferase, or a nucleic acid encoding it, can be about 70%, 75%, 80%, 85%, 90%, 95%, 96%, 97%, 98%, or 99% homologous to LgtB of a species of *Neisseria* (e.g., LgtB of *N. meningitidis*, LgtB of *N. gonorrhoeae*, or LgtE of *N. meningitidis*), CgtB of *C. jejuni*, WaaX of *E. coli*, HP0826 of *Helicobacter pylori*, or a eukaryotic β4Gal-T1.

Sialyltransferases

Any sialyltransferase, or nucleic acid encoding it, capable of adding one or more sialic acid residues to the monosaccharide (e.g., galactose) linked to the glucose that is linked to the Asn residue (or other relevant residue) in an N-glycosylation consensus sequence, e.g., Asn-X-Ser(Thr), wherein X can be any amino acid except Pro, can be used in accordance with the methods described herein, e.g., can be incorporated in a host cell described herein.

In certain embodiments, the sialyltransferase produces a target protein comprising alpha-2,3-linked or alpha-2,6-linked Neu5Ac.

In a specific embodiment, said sialyltransferase from a species of *Campylobacter*. In a specific embodiment, said sialyltransferase is CstII of *C. jejuni*. In another specific embodiment, said sialyltransferase is CstI of *C. jejuni*. In another specific embodiment, said sialyltransferase is Lst of *N. meningitidis*. In another specific embodiment, said sialyltransferase is Lst of *N. gonorrhoeae*.

In certain embodiments, the sialyltransferase is one that is homologous to a sialyltransferase of *Neisseria* or *Campylobacter*. For example, the sialyltransferase, or nucleic acid encoding it, is about 70%, 75%, 80%, 85%, 90%, 95%, 96%, 97%, 98%, or 99% homologous to CstII of *C. jejuni*, CstI of *C. jejuni*, Lst of *N. meningitidis*, or Lst of *N. gonorrhoeae*.

Polysialyltransferases

Any polysialyltransferase, or nucleic acid encoding it, capable of synthesizing polysialic acid (e.g., using the sialic acid residues added by a sialyltransferase as a starting point), can be used in accordance with the methods described herein, e.g., can be incorporated in a host cell described herein.

In a specific embodiment, said polyST is a polyST of *N. meningitidis*. In a specific embodiment, said polyST of *N. meningitidis* is a polyST of *N. meningitidis* serogroup B. In another specific embodiment, said polyST is a polyST of *E. coli* K1, *Mannheimania haemolytica*, or *Moraxella nonliquifacien*.

In certain embodiments, the polysialyltransferase is one that is homologous to a polysialyltransferase of a species of *Neisseria*, a species of *Mannheimania*, a species of *Moraxella*, or *E. coli*. For example, the polysialyltransferase, or a nucleic acid encoding it, is about 70%, 75%, 80%, 85%, 90%, 95%, 96%, 97%, 98%, or 99% homologous to the polyST of *N. meningitidis* serogroup B, the polyST of *Mannheimania haemolytica*, the polyST of *Moraxella nonliquifacien*, or the polyST of *E. coli*.

CMP-Neu5Ac Synthetases

Any CMP-Neu5Ac synthetase, or nucleic acid encoding it, known in the art can be used in accordance with the host cells and methods described herein. In a specific embodiment, the CMP-Neu5Ac synthetase is SynB of *N. meningitidis*.

In certain embodiments, the CMP-Neu5Ac synthetase is one that is homologous to a CMP-Neu5Ac synthetase of a species of *Neisseria*. For example, the CMP-Neu5Ac synthetase, or a nucleic acid encoding it, is about 70%, 75%, 80%, 85%, 90%, 95%, 96%, 97%, 98%, or 99% homologous to SynB of *N. meningitidis*.

Accessory Enzymes

In certain embodiments, nucleic acids encoding one or more accessory enzymes are introduced into the modified host cells described herein. Such nucleic acids encoding one or more accessory enzymes can be either plasmid-borne or integrated into the genome of the host cells described herein. Exemplary accessory enzymes include, without limitation, epimerases (see, e.g., International Patent Application Publication No. WO 2011/062615), branching, modifying, acetylating, formylating, polymerizing enzymes.

Genetic Background

In certain embodiments, the host cell genetic background is modified by, e.g., deletion or functional inactivation of one or more genes.

Exemplary genes that can be deleted/inactivated in host cells (and, in some cases, replaced with other desired nucleic acid sequences) include nanA and lacZ.

In a specific embodiment, the host cells provided herein comprise a deletion or functional inactivation of nanA. In another specific embodiment, the host cells provided herein comprise a deletion or functional inactivation of lacZ. In another specific embodiment, the host cells provided herein comprise a deletion or functional inactivation of nanA and lacZ.

5.2 Introduction of Nucleic Acids into Host Cells

Any method known in the art can be used to introduce a nucleic acid (e.g., a gene or an operon) into the a host cell, e.g., *E. coli*.

In specific embodiments, heterologous nucleic acids are introduced into the host cells described herein using a plasmid, e.g., the heterologous nucleic acids are expressed in the host cells by a plasmid (e.g., an expression vector), and the plasmid is introduced into the modified host cells by electroporation, chemical transformation by heat shock, natural transformation, phage transduction, or conjugation.

5.3 Methods of Glycosylated Target Protein Production

Provided herein are methods for producing glycosylated target proteins, including sialylated and polysialylated proteins, both in vivo and in vitro.

In one embodiment, provided herein is a method of producing glycosylated target proteins in vitro, said method comprising (i) using an NGT to add a glucose to a target protein that comprises one or more of N-glycosylation consensus sequences; (ii) using a glycosyltransferase (e.g., a galactosyltransferase) to add a monosaccharide (e.g., galactose) to said glucose; and (iii) using one or more additional glycosyltransferases to generate an oligosaccharide or polysaccharide on the glucose-monosaccharide primer.

In another embodiment, provided herein is a method of producing glycosylated target proteins in vivo, using a host cell described herein. In a specific embodiment, provided herein is a method for producing glycosylated target proteins, said method comprising (i) culturing a host cell provided herein under conditions suitable for protein production and (ii) isolating said target protein. In a specific embodiment, said host cell comprises (a) a nucleic acid that encodes a target protein comprising an N-glycosylation consensus sequence, e.g., Asn-X-Ser(Thr), wherein X can be any amino acid except Pro; (b) a nucleic acid that encodes an N-glycosyltransferase (NGT) that adds glucose to the Asn residue (or other relevant residue) present in said N-glycosylation consensus sequence, and (c) a nucleic acid that encodes a glycosyltransferase that catalyzes addition of a monosaccharide to said glucose, wherein at least one, two, or all of said target protein, said NGT, and said glycosyltransferase that catalyzes addition of a monosaccharide to said glucose are heterologous to the host cell. In another specific embodiment, said host cell is *E. coli*. In another specific embodiment, said NGT is the NGT of *Actinobacillus pleuropneumoniae*. In another specific embodiment, said nucleic acid that encodes a glycosyltransferase that catalyzes addition of a monosaccharide to said glucose present in the host cells provided herein encodes a galactosyltransferase, e.g., LgtB of *N. meningitidis*.

In another specific embodiment, provided herein is a method for producing sialylated target proteins, said method comprising (i) culturing a host cell provided herein under conditions suitable for protein production and (ii) isolating said target protein. In a specific embodiment, said host cell comprises (a) a nucleic acid that encodes a target protein comprising an N-glycosylation consensus sequence, e.g., Asn-X-Ser(Thr), wherein X can be any amino acid except Pro; (b) a nucleic acid that encodes an N-glycosyltransferase (NGT) that adds glucose to the Asn residue (or other relevant residue) present in said N-glycosylation consensus sequence, (c) a nucleic acid that encodes a glycosyltransferase that catalyzes addition of a monosaccharide to said glucose; and (d) a nucleic acid that encodes a sialyltransferase, wherein one, two, three, or all of said target protein, said NGT, said sialyltransferase, and said glycosyltransferase that catalyzes addition of a monosaccharide to said glucose are heterologous to the host cell. In another specific embodiment, said host cell is *E. coli*. In another specific embodiment, said NGT is the NGT of *Actinobacillus pleuropneumoniae*. In another specific embodiment, said nucleic acid that encodes a glycosyltransferase that catalyzes addition of a monosaccharide to said glucose present in the host cells provided herein encodes a galactosyltransferase, e.g., LgtB of *N. meningitidis*. In another specific embodiment, said sialyltransferase is CstII of *C. jejuni*.

In another specific embodiment, provided herein is a method for producing polysialylated target proteins, said method comprising (i) culturing a host cell provided herein under conditions suitable for protein production and (ii) isolating said target protein. In a specific embodiment, said host cell comprises (a) a nucleic acid that encodes a target protein comprising an N-glycosylation consensus sequence, e.g., Asn-X-Ser(Thr), wherein X can be any amino acid except Pro; (b) a nucleic acid that encodes an N-glycosyltransferase (NGT) that adds glucose to the Asn residue (or other relevant residue) present in said N-glycosylation consensus sequence, (c) a nucleic acid that encodes a glycosyltransferase that catalyzes addition of a monosaccharide to said glucose; (d) a nucleic acid that encodes a sialyltransferase; and (e) a nucleic acid that encodes a polysialyltransferase (polyST). In a specific embodiment, one, two, three, four, or all of said target protein, said NGT, said sialyltransferase, said polyST, and said glycosyltransferase that catalyzes addition of a monosaccharide to said glucose are heterologous to the host cell. In another specific embodiment, said host cell is *E. coli*. In another specific embodiment, said NGT is the NGT of *Actinobacillus pleuropneumoniae*. In another specific embodiment, said nucleic acid that encodes a glycosyltransferase that catalyzes addition of a monosaccharide to said glucose present in the host cells provided herein encodes a galactosyltransferase, e.g., LgtB of *N. meningitidis*. In another specific embodiment, said sialyltransferase is CstII of *C. jejuni*. In another specific embodiment, said polyST is a polyST of *N. meningitidis* (e.g., the polyST of *N. meningitidis* serogroup B).

In another specific embodiment, provided herein is a method for producing polysialylated target proteins, said method comprising (i) culturing a host cell provided herein under conditions suitable for protein production and (ii) isolating said target protein. In a specific embodiment, said host cell comprises (a) a nucleic acid that encodes a target protein comprising an N-glycosylation consensus sequence, e.g., Asn-X-Ser(Thr), wherein X can be any amino acid except Pro; (b) a nucleic acid that encodes an N-glycosyltransferase (NGT) that adds glucose to the Asn residue (or other relevant residue) present in said N-glycosylation consensus sequence, (c) a nucleic acid that encodes a glycosyltransferase that catalyzes addition of a monosaccharide to said glucose; (d) a nucleic acid that encodes a sialyltransferase; (e) a nucleic acid that encodes a polysialyltransferase (polyST); and (f) a nucleic acid that encodes a CMP-Neu5Ac synthetase. In a specific embodiment, one, two, three, four, five, or all of said target protein, said NGT, said sialyltransferase, said polyST, said CMP-Neu5Ac synthetase, and said glycosyltransferase that catalyzes addition of a monosaccharide to said glucose are heterologous to the host cell. In another specific embodiment, said host cell is *E. coli*. In another specific embodiment, said NGT is the NGT of *Actinobacillus pleuropneumoniae*. In another specific embodiment, said nucleic acid that encodes a glycosyltransferase that catalyzes addition of a monosaccharide to said glucose present in the host cells provided herein encodes a galactosyltransferase, e.g., LgtB of *N. meningitidis*. In another specific embodiment, said sialyltransferase is CstII of *C. jejuni*. In another specific embodiment, said polyST is a polyST of *N. meningitidis* (e.g., the polyST of *N. meningitidis* serogroup B). In another specific embodiment, said CMP-Neu5Ac synthetase is SynB of *N. meningitidis*.

In certain embodiments, when the host cells provided herein are used to produce sialylated and/or polysialylated proteins, the host cells are cultured in medium supplemented with Neu5Ac.

In certain embodiments, the target protein produced by the host cells provided is a therapeutic protein, i.e., a protein used in the treatment of a disease or disorder. For example, the target protein produced by the host cells provided herein can be an enzyme, a cytokine, or an antibody, wherein said target protein has been glycosylated, e.g., sialylated. A non-limiting list of target proteins is provided in Section 5.4, below.

5.4 Target Proteins

Any protein (or peptide/polypeptide corresponding to the protein) known in the art can be used as a target protein in accordance with the methods described herein. One of skill in the art will readily appreciate that the nucleic acid sequence of a known protein, as well as a newly identified protein, can easily be deduced using methods known in the art, and thus it would be well within the capacity of one of skill in the art to introduce a nucleic acid that encodes any protein of interest into a host cell provided herein (e.g., via an expression vector, e.g., a plasmid). One of skill in the art will further recognize that the target proteins glycosylated using the methods described herein, e.g., either in vivo using a host cell provided herein or in vitro, possess therapeutic benefit (e.g., due to improved pharmacokinetics) and thus can be used in the treatment of subjects having diseases/disorders that will benefit from treatment with the glycosylated (e.g., polysialylated) target proteins. Specifically, diseases and disorders that are caused by the presence of a defective version of a target protein in a subject, the absence of a target protein in a subject, diminished expression of a target protein in a subject can be treated or prevented using the glycosylated (e.g., polysialylated) target proteins produced using the methods described herein. In addition, diseases mediated by a receptor that is bound by a target protein produced using the methods described herein, or mediated by a ligand that is bound by a target protein produced using the methods described herein (e.g., where the target protein is a receptor for the ligand) can be treated using the glycosylated (e.g., polysialylated) target proteins produced using the methods described herein.

In a specific embodiment, the target protein used in accordance with the methods and host cells described herein is a therapeutic protein. Exemplary therapeutic proteins include enzymes, cytokines, hormones, growth factors, inhibitor proteins, protein receptors, ligands that bind protein receptors, and antibodies.

In a specific embodiment, the target protein used in accordance with the methods and host cells described herein is an enzyme or an inhibitor. Exemplary enzymes and inhibitors that can be used as a target protein include, without limitation, Factor VII, Factor VIII, Factor IX, Factor X, Factor XIII, Factor VIIa, Antithrombin III (AT-III), Protein C, Tissue plasminogen activator (tPA) and tPA variants, Urokinase, Hirudin, Streptokinase, Glucocerebrosidase, Alglucosidase-α, Laronidase (α-L-iduronidase), Idursulphase (Iduronate-2-sulphatase), Galsulphase, Agalsidase-β (human α-galactosidase A), Botulinum toxin, Collagenase, Human DNAse-I, Hyaluronidase, Papain, L-Asparaginase, Uricase (Urate oxidase), glutamate carboxypeptidase (glucarpidase), α1 Protease inhibitor (α1 antitrypsin), Lactase, Pancreatic enzymes (lipase, amylase, protease), and Adenosine deaminase.

In a specific embodiment, the target protein used in accordance with the methods and host cells described herein is a cytokine. Exemplary cytokines that can be used as a target protein include, without limitation, Interferon-α (INF-α), Interferon-β (INF-β), Interferon-γ (INF-γ), Interleukin-2 (IL2), Chimeric diphteria toxin-IL-2 (Denileukin diftitox), Interleukin-1 (IL1), IL1B, IL3, IL4, IL11, IL21, IL22, IL1 receptor antagonist (anakinra), and Tumor necrosis factor alpha (TNF-α).

In a specific embodiment, the target protein used in accordance with the methods and host cells described herein is a hormone or growth factor. Exemplary hormones and growth factors that can be used as a target protein include, without limitation, Insulin, Pramlintide, Growth hormone (GH), Insulin-like growth factor (IGF1), Human parathyroid hormone, Calcitonin, Glucagon-like peptide-1 agonist (GLP-1), Glucagon, Growth hormone-releasing hormone (GHRH), Secretin, Thyroid stimulating hormone (TSH), Human bone morphogenic protein 2 (hBMP2), Human bone morphogenic proetin 7 (hBMP7), Gonadotropin releasing hormone (GnRH), Keratinocyte growth factor (KGF), Platelet-derived growth factor (PDGF), Fibroblast growth factor 7 (FGF7), Fibroblast growth factor 20 (FGF20), Fibroblast growth factor 21 (FGF21), Epidermal growth factor (EGF), Vascular endothelial growth factor (VEGF), Neurotrophin-3, Human follicle-stimulating hormone (FSH), Human chorionic gonadotropin (HCG), Lutropin-α, Erythropoietin, Granulocyte colony-stimulating factor (G-CSF), and Granulocyte-macrophage colony-stimulating factor (GM-CSF).

In a specific embodiment, the target protein used in accordance with the methods and host cells described herein is an antibody. Exemplary antibodies that can be used as a target protein include, without limitation, antibodies that bind TNF-α, e.g., adalimumab (Humira) and Remicade (Infliximab); ReoPro (Abciximab); Rituxan (Rituximab); Simulect (Basiliximab); Synagis (Palivizumab); Herceptin (Trastuzumab); Mylotarg (Gemtuzumab ozogamicin); Campath (Alemtuzumab); Zevalin (Ibritumomab tiuxetan); Xolair (Omalizumab); Bexxar (Tositumomab-I-131); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab).

In a specific embodiment, the target protein used in accordance with the methods and host cells described herein is a receptor. Exemplary receptors that can be used as a target protein include, without limitation, the extracellular domain of human CTLA4 (e.g., fused to an Fc) and the soluble TNF receptor (e.g., fused to an Fc).

5.5 Compositions

Compositions Comprising Host Cells

In one aspect, provided herein are compositions comprising the host cells described herein (see Section 5.1). Such compositions can be used in methods for generating the glycosylated target proteins described herein (see Section 5.4), e.g., the compositions comprising host cells can be cultured under conditions suitable for the production of proteins. Subsequently, glycosylated target proteins can be isolated from said compositions comprising host cells using methods known in the art.

The compositions comprising the host cells provided herein can comprise additional components suitable for maintenance and survival of the host cells described herein, and can additionally comprise additional components required or beneficial to the production of proteins by the host cells, e.g., inducers for inducible promoters, such as arabinose, IPTG.

Compositions Comprising Glycosylated Target Proteins

In another aspect, provided herein are compositions (e.g., pharmaceutical compositions) comprising one or more of the glycosylated target proteins described herein (see Section 5.4). The compositions described herein are useful in the treatment and/or prevention of diseases/disorders in subjects (e.g., human subjects). See Section 5.6.

In a specific embodiment, provided herein is a composition comprising glycosylated target proteins produced using a host cell described herein, wherein at least 80%, 85%, 90%, 95%, or 99% of the N-glycosylation consensus sequences present in said proteins comprise a glucose linked to the Asn residue (or other relevant residue) present in the N-glycosylation consensus sequence.

In another specific embodiment, provided herein is a composition comprising glycosylated target proteins produced using a host cell described herein, wherein at least 80%, 85%, 90%, 95%, or 99% of the N-glycosylation consensus sequences present in said proteins comprise an identical attached polysaccharide linked to the Asn residue (or other relevant residue) present in said N-glycosylation consensus sequences.

In another specific embodiment, provided herein is a composition comprising glycosylated target proteins produced using a host cell described herein, wherein at least 80%, 85%, 90%, 95%, or 99% of the proteins in said composition have been N-glycosylated by the NGT of said host cell, e.g., an NGT encoded by a heterologous nucleic acid present in said host cell. In a specific embodiment, at least 80%, 85%, 90%, 95%, or 99% of the N-glycosylation consensus sequences present in each protein present in said composition comprise a glucose linked to the Asn residue (or other relevant residue) present in said N-glycosylation consensus sequences. In another specific embodiment, at least 80%, 85%, 90%, 95%, or 99% of the N-glycosylation consensus sequences present in each protein present in said composition comprise an identical attached polysaccharide linked to the Asn residue (or other relevant residue) present in said N-glycosylation consensus sequences.

In another specific embodiment, provided herein is a composition comprising sialylated proteins produced using a host cell described herein. In a specific embodiment, at least 80%, 85%, 90%, 95%, 96%, 97%, 98%, or 99% of said proteins in said composition are sialylated or polysialylated. In another specific embodiment, 100% of said proteins in said composition are sialylated or polysialylated. In another specific embodiment, at least 80%, 85%, 90%, 95%, or 99% of the N-glycosylation consensus sequences present in each protein present in said composition comprise an identical sialylation pattern at the Asn residue (or other relevant residue) present in said N-glycosylation consensus sequences.

In certain embodiments, in addition to comprising a glycosylated target protein described herein (see Section 5.4), the compositions (e.g., pharmaceutical compositions) described herein comprise a pharmaceutically acceptable carrier. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier," as used herein in the context of a pharmaceutically acceptable carrier, refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin.

In certain embodiments, the compositions described herein are formulated to be suitable for the intended route of administration to a subject. For example, the compositions described herein may be formulated to be suitable for subcutaneous, parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, the compositions described herein additionally comprise one or more buffers, e.g., phosphate buffer and sucrose phosphate glutamate buffer. In other embodiments, the compositions described herein do not comprise buffers.

In certain embodiments, the compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the compositions described herein do not comprise salts.

The compositions described herein can be included in a kit, container, pack, or dispenser together with instructions for administration.

The compositions described herein can be stored before use, e.g., the compositions can be stored frozen (e.g., at about −20° C. or at about −70° C.); stored in refrigerated conditions (e.g., at about 4° C.); or stored at room temperature.

5.6 Prophylactic and Therapeutic Uses

In one aspect, provided herein are methods of treating a disease or disorder in a subject comprising administering to the subject a glycosylated target protein described herein (see Section 5.4) or a composition thereof (see Section 5.5). In another aspect, provided herein are methods of preventing a disease or disorder in a subject comprising administering to the subject a glycosylated target protein described herein (see Section 5.4) or a composition thereof (see Section 5.5). In a specific embodiment, provided herein is a method for treating or preventing a disease or disorder in a subject comprising administering to the subject a polysialylated target protein produced according to the methods described herein.

6. EXAMPLES

6.1 Materials and Methods

Plasmid Design and Construction.

Plasmids incorporating various components required for NGT-mediated protein glycosylation in host cells were created. In particular, plasmids harboring *Actinobacillus pleuropneumoniae* ngt (ApNGT), lgtB of *Neisseria meningitidis* (MC58), cstII of *Campylobacter jejuni* (strain OH4382/84, containing a C-terminal 32-amino acid deletion and an I53S mutation, (see Chiu C. P. et al., Nat Struct Mol Biol. 2004 February; 11(2):163-70)), either siaB (or synB, CMP-Neu5Ac synthase) alone or in addition with siaA (or synX, UDP-N-acetylglucosamine 2-epimerase) and siaC (or synC, sialic acid synthase), all from *Neisseria meningitidis* (MC58) and/or polyST from *Neisseria meningitidis* serogroup B (F116-polyST$_{F460T}$, see Keys T. G. et al., Nat Chem Biol. 2014 Jun; 10(6):437-42, with an N-terminal Strep-tag) or polyST from *Mannheimia haemolytica* (with an N-terminal deletion of 20 amino acids, see Lindhout at al., PLoS One 2013 8(7):e69888. doi: 10.1371/journal.pone.0069888) were constructed. Different combinations were generated to assess N-glycosylation efficiency. See Table 1 and below.

The amino acid sequence for each protein in the pathway was back-translated using the GENEius server at the GENEius website and codon optimized using codon usage designed to give a codon bias closely approximating the average of Freq-A, -B and -C published by DNA2.0 (see Welch et al. PLoS ONE 4, e7002 (2009)), and avoiding common restriction sites and extended single base repeats (see Table 2). Genes in the sialyllactose pathway were organized into a pseudo-operon architecture (see Xu P. et al., ACS Synth. Biol. 1,256-266 (2012), Xu P. et al., Nat. Commun. 4, 1409 (2013), and He W. et al., Metab. Eng. 27 92-100 (2015)), with each gene placed under the control of a lacUV5 promoter including the lac operator (see Deuschle et al., EMBO J. 5, 2987-2994 (1986)) and a custom ribosome binding site designed by the Salis Lab RBS Calculator at the Salis Lab website with a target translation initiation rate of approximately 50,000 a.u. (see Espah Borujeni A et al. Nucleic Acid Res, 42(4), 2646-59 (2014) and Farasat I et al. Mol Syst Biol, 10, 731 (2014)). The siaABC genes occur as part of a polycistronic operon encoding biosynthesis of the polysialic acid capsule in *Neisseria meningitidis* serogroup B. These genes were taken as a block, together with their native RBSs, and placed under the control of a lacUV5 promoter including the lac operator. The operon is followed by a single translation termination site. Two sets of isocaudamer restriction sites, which leave complimentary overhangs, were used to flank each gene to allow for facile modification of the pathway, including deletion of genes and exchanging of regulatory elements. Constructs encoding the NGT-mediated protein glycosylation pathway were synthesized (GENEWIZ Inc.) and introduced into the pUC57 vector or pACYC-Duet vector (Novagen) or pCDF-Duet vector (Novagen). Further plasmid manipulations, including sub-cloning into different plasmid backbones, as well as insertions and deletions of genes and tags, was carried out using standard molecular biology techniques. All constructs were sequenced to confirm the desired modification.

Bacterial Strains and Growth Conditions.

The *E. coli* DH5a strain was used for maintenance and propagation of plasmid DNA. The *E. coli* K12 derivative JM107 ΔnanA:kan strain (see Priem et al., Glycobiology. 12, 235-240 (2002)) was used as the host strain for the glycosylation experiments. Unless otherwise noted, bacteria were grown in Luria-Bertani (LB) medium in shaker flasks or on LB plates containing 1.5% (w/v) agar. Where appropriate, media was supplemented with antibiotics at the following concentrations: Ampicillin 100 µg/ml, Chloramphenicol 35 µg/ml, Spectinomycin 50 µg/ml, and Trimethoprim 50 µg/ml. For production of (poly)sialylated proteins using bacterial strains expressing only SiaB, i.e. using the scavenger pathway for CMP-Neu5Ac biosynthesis (see FIG. 1), the media was supplemented with 5 mM Neu5Ac. Cultures were grown at 37° C. to an OD600 of approximately 1.0 (or 1.8-2.0 for polysialylation of proteins) and expression was induced by the addition of 1 mM IPTG and 0.4% L-arabinose. Cultures were grown for a further 20-24 hours at 28° C. in the presence of inducing reagents. Cell pellets were harvested by centrifugation then washed once with PBS prior to storage at −20° C. until further processing.

The *E. coli* K12 derivative W3110 ΔlacZ ΔnanA ΔnanK was used as the host for glycosylation experiments with pathway constructs encoding the genes for de novo synthesis of CMP-Neu5Ac, siaABC (pLMTB4250). See FIG. 1. Unless otherwise noted, bacteria were cultivated as described above, however, the media was not supplemented with Neu5Ac, and expression was induced when cultures were grown to an OD600 of approximately 0.6-1.0.

Small Scale Preparation and Enrichment of Proteins for Glycosylation Analysis.

The cell pellet from a 10 ml expression culture was resuspended in approximately 650 µl of lysis buffer (60 mM Tris pH 8.0, 1 mM MgCl$_2$) and supplemented with 1 mg/ml of lysozyme and 20 µg/ml of DNaseI. Cells were lysed by three cycles of freeze-thaw-sonication consisting of i) snap freezing in liquid N$_2$, ii) 5 min thawing in a sonication bath at room temperature, and iii) 15 min at room temperature. Cellular debris was pelleted at 20,000 g and the supernatant (the cell free extract) was either analyzed directly, or the protein of interest was enriched via NiNTA beads and/or StrepTactin Sepharose as follows.

For enrichment of scAtaC, supernatants were supplemented with protease inhibitor cocktail (Sigma), and adjusted to 20 mM Tris pH 8.0, 300 mM NaCl and 6 M urea (binding buffer) in a final volume of 2 ml. The 6xHis tagged AtaC samples were bound to NiNTA beads in batches, then loaded onto a mini-column, washed with 30 mM imidazole in binding buffer, and eluted with 200 mM imidazole in binding buffer. The eluent was concentrated to approximately 200 µl using a centrifugal concentrator (Amicon) with 30 kDa cutoff.

For enrichment of GFP constructs, cell lysates were supplemented with protease inhibitor cocktail (Sigma), and bound directly on NiNTA beads in batch format. Beads were loaded onto a mini-column, washed with 30 mM imidazole in 60 mM Tris pH 8.0, and eluted with 250 mM imidazole in 60 mM Tris pH 8.0. The eluent was loaded directly onto pre-equillibrated StrepTactin Sepharose beads, washed with 60 mM Tris pH 8.0, and eluted with 2.5 mM desthiobiotin. Samples were concentrated and buffer exchanged into PBS for storage.

Samples were analysed by SDS-PAGE followed by immunoblot with anti-His4 antibodies (Qiagen), N-Hexose reactive human serum MS14 (see Naegeli et al., J. Biol. Chem. 289, 2170-2179 (2014); and Lolli et al., Proc. Natl. Acad. Sci. U.S.A 102, 10273-10278 (2005)) and anti-polysialic acid monoclonal antibody 735 (Absolute Antibody) or were analysed by tryptic digest followed by nano-LC-ESI-MS/MS.

Purification of Polysialylated GFP.

The cell pellet from 1 liter expression culture (approximately 13 g wet weight) was resuspended in 35 ml of Lysis buffer (20 mM Tris pH 7.0, 2 mM beta-mercaptoethanol, 1 mM $MgCl_2$, 100 µg/ml DNaseI, protease inhibitor cocktail). Cells were lysed by three passages through a French Press and clarified by centrifugation at 20,000 g for 30 min at 4° C. The supernatant was passed over an NiNTA column, washed with 20 mM imidazole in 20 mM Tris pH 7.0, 2 mM beta-mercaptoethanol, and eluted with 250 mM imidazole in the same buffer. The eluent was concentrated and loaded directly on a 2 ml MonoQ column pre-equillibrated with buffer A (20 mM Tris pH 7.0, 2 mM beta-mercaptoethanol), washed for 15 min, then eluted in a gradient from 0-100% buffer B (1 M NaCl, 20 mM Tris pH 7.0, 2 mM beta-mercaptoethanol) over 70 min at a flow rate of 1 ml/min. UV absorbance at 280 nm was monitored online, and GFP containing fractions were identified by measuring fluorescence (Ex. 485 nm/Em. 520 nm) of each fraction using a microtiterplate fluorescence spectrometer. Three GFP containing fractions (low, medium, and high salt) were pooled, exchanged into storage buffer (60 mM Tris pH 7.0, 100 mM NaCl, 2 mM beta-mercaptoethanol and 10% glycerol), concentrated, and frozen for further analysis. Protein concentrations were determined by BCA assay (Pierce) and GFP fluorescence measurements.

Purification of Polysialylated

VEGF-A-antagonistic designed ankyrin repeat protein (DARPin). Biomass corresponding to an OD600 of 500,000 was resuspended in 3000 ml of binding buffer (10 mM imidazole, 30 mM Tris pH 7.0, 500 mM NaCl). Cells were lysed by one passage through a Microfluidizer LM20 at 20,000 PSI and clarified by centrifugation at 10,000 g for 1 h at 4° C. The supernatant was loaded onto a 200 ml XK50/20 column (GE) packed with Toyopearl AF-Chelate-650M (Tosoh) resin at a flow rate of 10 ml/min. The column was washed with 40 column volumes (CV) of endotoxin removal buffer (10 mM imidazole, 30 mM Tris pH 8.0, 500 mM NaCl, 0.1% Triton X-114), followed by 40 CV of wash buffer (10 mM imidazole, 30 mM Tris pH 7.0, 500 mM NaCl) and finally eluted in a gradient from 10 mM to 500 mM imidazole in 30 mM Tris pH 7.0, 100 mM NaCl over 15 CV at a flow rate of 10 ml/min. Fractions containing polysialylated DARPin were pooled and loaded onto a 30 ml×16 HiScale column (GE) packed with Source15Q resin (GE). Subsequently, the column was washed with 5 CV of wash buffer (30 mM Tris pH 7.0, 100 mM NaCl) and eluted in a gradient from 100 mM to 350 mM NaCl in 30 mM Tris pH 7.0 over 40 CV. Three DARPin containing fractions (corresponding to low, medium, and high salt) were pooled, concentrated, and loaded onto a 318 ml Superdex 200 26/60 prep grade column in 1×PBS pH 7.5 at a flow rate of 2.5 ml/min. The fractions containing DARPin from the final size exclusion chromatography step were concentrated to 2 mg/ml (determined by BCA assay (Pierce)), supplemented with a protease inhibitor cocktail (Roche), sterilized by filtration, and then frozen for further analysis.

Analytical Anion Exchange Chromatography.

Purified glycoproteins were diluted to 1 mg/ml in 20 mM Tris pH 7.0. Approximately 4 µg of protein was loaded directly on a ProPac SAX column (Dionex) and separated in a gradient from 50 to 600 mM NaCl in 20 mM Tris pH 7.0 over 15 min at a flow rate of 1.2 ml/min. Absorbance at 280 nm and GFP fluorescence (Ex. 485 nm/Em 520 nm) were monitored online.

Analytical Size Exclusion Chromatography.

Purified proteins were diluted to 100 µg/ml in 1×PBS pH7.5. Approximately 5 µg of protein was loaded directly on an Agilent Bio SEC-5 column. The samples were run isocratic in 1×PBS pH 7.5 at a flow rate of 0.6 ml/min. Absorbance at 215 nm was monitored online. A Bio-Rad gel filtration standard (Catalog#151-1901) was used.

Surface Plasmon Resonance Spectroscopy.

The kinetic parameters of the VEGF-binders were measured using a Biacore T200 instrument at 25° C. The bait ligand (recombinant human $VEGF_{165}$, Acro Biosystems) was covalently immobilized on a sensor chip C1 surface at three different densities. The prey analyte (different DARPins, or as a positive control, recombinant human VEGF-R1 (Acro Biosystems)) was analysed using multi cycle kinetics in 10 mM HEPES pH 7.4, 150 mM NaCl, 3 mM EDTA, 0.05% Tween 20 at a flow rate of 50 µl/min.

Nano-LC-ESI-MS/MS Analysis.

Samples were prepared for mass spectrometric analysis using the filter aided method (see Wisniewski et al., Nat. Methods 6, 359-362 (2009)) and peptides were concentrated and desalted with a C18 ZipTip (Millipore). Sample analysis was performed with a calibrated LTQ-Orbitrap Velos mass spectrometer (ThermoFischer Scientific) coupled to a Nano-HPLC (Eksigent Technologies). Peptides were resuspended in 2.5% acetonitrile, 0.1% formic acid (FA), loaded on a self-made fitted column (75 µm×150 mm) packed with reverse phase C18 material (ReproSil-Pur 120 C18-AQ, 1.9 µm, Dr. Maisch GmbH, Germany) and eluted with a flow rate of 300 nl/min using three linear gradients steps: from 3% to 30% acetonitrile in 22 min, from 30% to 50% acetonitrile in 25 min, and from 50% to 97% acetonitrile in 27 min, with constant 0.1% formic acid. One scan cycle comprised of a full scan MS survey spectrum, followed by up to 10 sequential HCD MS/MS on the most intense signals above a threshold of 2000. Full scan MS spectra (500-2000 m/z) were acquired in the FT-Orbitrap at a resolution of 60,000 at m/z 400. HCD MS/MS spectra were recorded in the Orbitrap (target value 1e5, collision energy 35 V) at a resolution of 15,000 at m/z 400. Auto gain control (AGC) target values were $1\times10^6$ for full FTMS scans and $1\times10^5$ for HCD MS/MS scans. For all experiments, dynamic exclusion was used with one repeat count, 15-s repeat duration, and 60-s exclusion duration.

Database Analysis and Identification of Modified Residues.

MS and MS/MS data were searched against the Swissprot database (version 201504) through the Mascot engine (version 2.4) with the consideration of carbamidomethylation at Cys, oxidation at Met and one/two Hexoses at Asn. The monoisotopic masses of 2+ or more charged peptides were searched with a peptide tolerance of 8 ppm and a MS/MS tolerance of 0.25 Da for fragment ions. The presence of oxonium ions for NeuAc (292.10) and $NeuAc-H_2O$ (274.09) in MS/MS spectra were used to scout for sialylated glycopeptides on one LC run. Sequencing of the peptide was performed manually.

TABLE 1

Bacterial strains and plasmids used

| Strain/plasmid | Genotype/description | Reference or source |
|---|---|---|
| Strains | | |
| DH5α | F- Φ80lacZΔM15 Δ(lacZYA-argF) U169 recA1 endA1 hsdR17 (rK–, mK+) phoA supEAA λ– thi-1 gyrA96 relA1 | Stratagene |
| JM107 nanA::kan | endA1 glnV44 thi-1 relA1 gyrA96 Δ(lac-proAB) [F' traD36 proAB+ lacIq lacZΔM15] hsdR17(RK– mK+) λ– nanA– | Priem et al. (2002) |
| StLMTB10758 | W3110 (E. coli genetic stock center CGSC #4474) ΔlacZ, ΔnanA, ΔnanK | This Example |
| Plasmids | | |
| pACYC-DUET | Cm$^R$, lacI, P15A ori | Novagen |
| pCDF-DUET | Spectinomycin$^R$, lacI, CloDF13 ori | Novagen |
| pMA885 | scAtaC expression vector; pMLBAD(scAtaC-His6); soluble AtaC fragment (aa1866-2428); C-terminal 6xHis-tag; pBAD promoter; Trimethoprim$^R$ | Naegeli et al. (2014) |
| pMA1045 | GlycoTag-GFP expression vector; pMLBAD(10xHis-sfGFP-GlycoTag-Strep); N-terminal 10x His-tag; C-terminal GlycoTag followed by Strep-tag; pBAD promoter; Trimethoprim$^R$. | This Example |
| pLMTB3724 | GlycoTag-DARPin expression vector; pMLBAD(10xHis-DARPin (anti-human VEGF)-GlycoTag-Strep); N-terminal 10x His-tag; C-terminal GlycoTag followed by Strep-tag; pBAD promoter; Trimethoprim$^R$. | This Example |
| pMA991 | "sialyllactose pathway" includes siaB, cstII$_{I53S}$Δ32, lgtB and ApNGT, each under control of a lacUV5 promoter; vector backbone is pACYC-DUET. | This Example |
| pMA992 | "lactose pathway" includes lgtB and ApNGT, each under control of a lacUV5 promoter; vector backbone is pACYC-DUET. | This Example |
| pMA993 | "N-Glc pathway" includes only the ApNGT, under control of a lacUV5 promoter; vector backbone is pACYC-DUET. | This Example |
| pMA1075 | Control pathway construct lacking the ApNGT. Includes siaB, cstII$_{I53S}$Δ32 and lgtB, each under control of a lacUV5 promoter; vector backbone is pACYC-DUET. | This Example |
| pLMTB4250 | "de novo sialyllactose pathway" includes siaABC (from N. meningitidis serogroup B), cstII$_{I53S}$Δ32, lgtB and ApNGT, each under control of a lacUV5 promoter; vector backbone is pACYC-DUET | This Example |
| pMA1059 | Polysialyltransferase expression construct. pCDF-DUET encoding Strep-F116-polyST$_{F460T}$; N-terminal Strep-tag; T5 promoter; Spectinomycin$^R$ | This Example |
| pLMTB3961 | Polysialyltransferase expression construct. pCDF-DUET encoding Δ20polyST from Mannheimia haemolytica; T5 promoter; Spectinomycin$^R$ | This Example |
| pLMTB3962 | Polysialyltransferase expression construct. pCDF-DUET encoding MalE-Δ20polyST from Mannheimia haemolytica; N-terminal MalE fusion; T5 promoter; Spectinomycin$^R$ | This Example |

TABLE 2

ApNGT Sequences

| SEQ ID NO. | |
|---|---|
| 1 (ApNGT amino acid sequence) | MENENKPNVANFEAAVAVKDYEKACSELLLILSQLDSNFGGIQEIEFEYPVQLQDLEQEK IVYFCTRMATAITTLFSDPVLEISDLGVQRFLVYQRWLALIFASSPFVNADHILQTYNRE PNRKNSLEIHLDSSKSSLIKFCILYLPESNVNLNLDVMWNISPELCASLCFALQSPRFIG TSTAFNKRATILQWFPRHLDQLKNLNNIPSAISHDVYMHCSYDTSVNKHDVKRALNHVIR RHIESEYGWKDRYVAHIGYRNNKPVMVVLLEHFHSAHSIYRTHSTSMIAAREHFYLIGLG SPSVDQAGQEVFDEFHLVAGDNMKQKLEFIRSVCESNGAAIFYMPSIGMDMTTIFASNTR LAPIQAIALGHPATTHSDFIEYVIVEDDYVGSEACFSETLLRLPKDALPYVPSALAPEKV DYLLRENPEVVNIGIASTTMKLNPYFLEALKAIRDRAKVKVHPHFALGQSNGITHPYVER FIKSYLGDSATAHPHSPYHQYLRILHNCDMMVNPFPFGNTNGIIDMVTLGLVGVCKTGAE VHEHIDEGLFKRLGLPEWLIANTVDEYVERAVRLAENHQERLELRRYIIENNGLNTLFTG DPRPMGQVFLEKLNAFLKEN |
| 2 (Wild type ApNGT nucleic acid sequence) | ATGGAAAACGAAAATAAACCGAATGTAGCTAATTTTGAAGCGGCGGTTGCGGTTAAAGAT TATGAAAAAGCTTGCTCCGAATTACTTTTAATTTTGAGTCAGTTAGACAGTAACTTTGGT GGTATTCAGGAGATTGAGTTTGAATATCCGGTGCAGCTTCAGGATTTAGAACAAGAAAAA ATAGTTTATTTTTGTACGCGTATGGCAACGGCGATTACTACGTTGTTTTCCGATCCTGTC TTAGAAATCTCCGATTTAGGCGTTCAGAGATTTTTGGTTTATCAACGTTGGTTAGCGTTA ATCTTTGCCAGTTCACCGTTTGTGAATGCGGATCATATATTACAAACATATAACAGAGAG CCGAATCGTAAGAATAGTTTAGAGATTCATTTAGATTCTTCAAAATCGTCATTAATTAAA TTCTGTATCCTGTATTTACCGGAATCTAACGTAAATTTGAATCTGGATGTAATGTGGAAT ATTTCACCTGAATTATGCGCTTCTTTATGTTTTGCTTTGCAATCGCCTCGTTTTATCGGT ACATCAACTGCGTTTAATAAACGAGCGACCATTTTGCAATGGTTTCCACGACATTTGGAT CAACTTAAAAACCTGAATAATATTCCTAGTGCCATTTCGCATGACGTATATATGCATTGT AGTTATGATACGTCAGTAAATAAACATGATGTGAAAAGGGCGTTAAATCATGTTATTCGT CGCCATATCGAAAGTGAATACGGTTGGAAAGATCGATATGTCGCTCATATCGGTTATCGT AATAATAAACCGGTTATGGTCGTATTACTGGAACATTTCCATTCGGCCCATTCTATTTAC CGTACGCATTCCACATCTATGATTGCGGCGCGTGAACATTTCTATTTAATCGGTTTAGGT |

TABLE 2-continued

ApNGT Sequences

| SEQ ID NO. | |
|---|---|
| | AGTCCGTCGGTTGATCAAGCGGGTCAAGAGGTTTTTGATGAGTTCCACTTGGTTGCCGGC |
| | GATAATATGAAGCAGAAGTTAGAATTTATCCGCTCAGTTTGTGAGAGCAACGGTGCCGCA |
| | ATATTTTATATGCCGAGTATCGGTATGGATATGACGACGATTTTCGCAAGTAATACGCGC |
| | CTTGCTCCGATACAAGCGATCGCATTGGGGCATCCGGCAACAACACATTCGGACTTCATT |
| | GAATATGTGATTGTGGAAGACGATTATGTCGGCTCGGAAGCGTGTTTTAGTGAAACATTA |
| | TTGCGCTTACCGAAAGACGCATTACCTTATGTTCCGTCAGCATTAGCACCTGAGAAGGTG |
| | GATTATTTATTACGTGAAAATCCGGAAGTGGTAAATATCGGTATAGCTTCAACCACGATG |
| | AAGCTAAATCCGTATTTCTTAGAAGCGTTAAAAGCGATTCGTGATCGTGCCAAAGTGAAA |
| | GTGCATTTCCATTTTGCATTGGGGCAATCAAACGGTATTACTCACCCGTATGTAGAACGC |
| | TTTATTAAATCTTATTTAGGTGATTCGGCCACTGCGCACCCTCATTCTCCTTATCATCAA |
| | TATCTCCGTATTTTGCATAATTGCGATATGATGGTAAACCCGTTCCCATTCGGGAATACG |
| | AACGGAATTATCGATATGGTCACTTTAGGCTTAGTTGGTGTGTAAGACAGGAGCCGAA |
| | GTTCATGAGCATATTGATGAAGGGCTGTTTAAACGTTTAGGCTTACCCGAGTGGCTGATA |
| | GCAAATACGGTAGATGAATATGTTGAACGGGCGGTTCGCTTAGCGGAAAATCATCAGGAG |
| | CGTTTAGAGTTACGTCGATATATTATTGAAAATAACGGATTGAACACATTGTTTACCGGG |
| | GATCCTAGACCGATGGGACAAGTATTTTTAGAAAAATTAAATGCGTTCCTAAAAGAAAAT |
| | TAA |
| 3<br>(Codon<br>Optimized<br>ApNGT<br>nucleic<br>acid<br>sequence) | ATGGAGAACGAGAATAAGCCTAATGTTGCAAACTTTGAGGCGGCAGTTGCTGTCAAAGAC<br>TACGAGAAGGCTTGCTCCGAGCTGTTGCTGATCTTGTCTCAGCTGGATAGCAACTTTGGC<br>GGTATTCAAGAAATCGAGTTCGAGTACCCGGTTCAACTCCAGGACCTCGAACAAGAGAAA<br>ATTGTATACTTCTGCACCCGCATGGCGACCGCGATCACGACCTTGTTTTCCGACCCTGTT<br>CTGGAGATCAGCGACCTGGGTGTTCAGCGTTTCCTGGTTTACCAACGTTGGCTCGCATTG<br>ATCTTTGCATCGTCCCCGTTTGTTAACGCGGATCATATTCTGCAAACCTATAACCGCGAA<br>CCGAACCGTAAAAACTCTTTGGAAATCCATCTGGACTCTAGCAAATCCAGCCTCATCAAA<br>TTTTGCATTTTATACTTGCCGGAGTCCAACGTCAACCTGAACTTGGACGTGATGTGGAAC<br>ATTAGCCCGGAGTTGTGCGCCAGCCTGTGCTTCGCACTGCAGTCGCCGCGCTTCATCGGC<br>ACCTCTACCGCGTTCAACAAGCGTGCGACTATTTTACAATGGTTTCCACGTCACCTGGAC<br>CAGCTGAAAAATTTGAACAACATTCCGAGCGCGATTTCCCACGACGTCTATATGCATTGC<br>TCTTACGACACCTCCGTGAACAAGCATGATGTCAAACGTGCGCTGAACCATGTGATTCGC<br>CGTCATATCGAGTCCGAATACGGCTGGAAAGACCGTTACGTGGCGCACATCGGCTACCGT<br>AACAACAAGCCGGTGATGGTTGTTCTGCTGGAGCACTTTCACTCTGCACACTCCATCTAT<br>CGTACCCACTCGACCTCCATGATTGCGGCCCGCGAGCACTTTTACCTGATCGGTTTGGGT<br>AGCCCGAGCGTTGATCAAGCGGGCCAAGAGGTTTTTGACGAGTTTCATCTCGTTGCGGGT<br>GATAATATGAAGCAGAAGCTGGAGTTCATTCGTTCGGTGTGCGAGTCTAACGGTGCCGCC<br>ATCTTCTACATGCCGTCCATTGGCATGGATATGACCACCATCTTCGCTTCGAATACTCGC<br>CTTGCGCCTATCCAGGCGATCGCACTGGGCCACCCTGCCACCACCCACAGCGACTTTATC<br>GAGTACGTCATCGTTGAGGACGATTACGTGGGCTCCGAGGCATGCTTTAGCGAAACGTTG<br>CTGAGACTGCCGAAGGACGCGCTGCCGTATGTCCCGTCCGCCTTGGCCCCGGAGAAAGTT<br>GATTATCTTTTGCGTGAGAATCCAGAGGTCGTTAATATTGGCATTGCGAGCACCACCATG<br>AAGCTGAACCCTTATTTCTTGGAAGCGCTGAAGGCGATCCGTGATCGTGCTAAAGTCAAA<br>GTTCACTTCCATTTTGCGCTGGGCCAAAGCAACGGTATTACCCATCCATACGTTGAGCGT<br>TTCATTAAGTCCTACCTGGGTGATAGCGCGACCGCTCACCCACATTCCCCGTATCACCAA<br>TACTTGCGCATCTTGCATAATTGCGACATGATGGTTAACCCGTTCCCGTTTGGTAACACG<br>AATGGCATCATTGATATGGTGACCCTCGGTCTGGTTGGTGTTTGCAAAACCGGTGCAGAG<br>GTCCACGAACACATCGACGAGGGCTTGTTTAAGCGTCTGGGCTTGCCGGAATGGCTGATT<br>GCCAACACCGTTGACGAATATGTGGAGCGTGCGGTGCGTTTGGCGGAAAACCACCAGGAA<br>CGCTTGGAGCTGCGCCGCTATATTATCGAGAATAATGCCTTGAATACGCTGTTTACCGGT<br>GACCCGCGTCCGATGGGTCAGGTTTTTCTGGAAAAATTGAACGCTTTCTTGAAGGAGAAC<br>TAA |

6.2 Example 1: Generation of a Host Cell Capable of Cytosolic Protein Glycosylation A cytoplasmic N-glycosylation system was recently elucidated in several species of gammaproteobacteria (Grass et al., PLoS Pathogen 6, e1000919 (2010) and Choi et al., PLoS ONE 5, e15888 (2010)). In these bacteria, a cytoplasmic N-glycosyltransferase (NGT) modifies asparagine residues in the Asn-X-Ser(Thr) sequon, and it does so using the simple nucleotide sugar UDP-glucose (UDP-Glc) as donor substrate. The resulting Glc β1-Asn modification is a simple molecular mimic of the eukaryotic N-glycan core structure (Schwarz et al., J. Biol. Chem. 286, 35267-35274 (2011)). It has previously been demonstrated that the NGT from *Actinobacillus pleuropneumoniae* (ApNGT) can be used to modify heterologous proteins in the cytoplasm of *E. coli* (Naegeli et al., J. Biol. Chem. 289, 2170-2179 (2014)). In this example, the ability of an ApNGT to glucosylate a target protein, wherein an N-linked glucose can be used to provide a site-specific handle (e.g., a primer) for bottom-up synthesis of novel N-linked glycans directly in the bacterial cytoplasm was demonstrated. In particular, the ability to generate a polysialylated protein in the *E. coli* cytosol, using the N-linked glucose as a primer for polysialylation, was demonstrated.

α2,8-linked polyisalic acid (polySia) is a linear homopolymer with distinct biological functions and broad biotechnological potential. In the human central nervous system, polySia is attached to the N-glycans of specific proteins where it promotes plasticity via its anti-adhesive properties (see Rutishauser et al., Nat Rev Neurosci 9, 26-35 (2008) and Hildebrandt et al., Top. Curr. Chem. (2013). Doi: 10.1007/128_2013_446). Additionally, lipid anchored polySia forms the extracellular capsule of several strains of neuroinvasive bacterial pathogens. The bacterial a2,8-linked polysaccharide is chemically and immunologically identical to human polySia and serves as a molecular mimic, camouflaging the antigen rich bacterial surface and facilitating immune evasion (see Troy F. A. et al. Glycobiology 2, 5-23 (1992)). In line with these biological functions, polySia has a number of biotechnological applications. Notably, polysialylation of protein therapeutics reduces immunogenicity and proteolytic degradation, and increases circulating half-life, and thus holds great potential as a natural and biodegradable alternative to PEGylation (chemical attachment of polyethylene glycol chains) of protein therapeutics (see Constantinou et al., Bioconjug. Chem. 19, 643-650 (2008) and Lindhout et al., Proc. Natl. Acad. Sci. U.S.A. 108, 7397-7402 (2011)). However, the available strategies for polysialylation of proteins are limited to chemoenzymatic extension of existing N-glycans (see Lindhout et al., Proc. Natl. Acad. Sci. U.S.A. 108, 7397-7402 (2011)) or chemical conjugation with the purified and functionalized polysaccharide (Smirnov et al., Glyco-Engineering (ed. Castilho, A.) 389-404 (Springer New York, 2015)). Biosynthesis has not been possible because eukaryotic polysialyltransferases (polyST) exhibit remarkable specificity for only a handful of protein targets (see Mühlenhoff et al., Neurochem. Res. 1-10 doi:10.1007/s11064-013-0979-2). This point is highlighted by a recent in planta glycoengineering study by Kallolimath et al. (Kallolimath et al., Proc. Natl. Acad. Sci. (2016). doi:10.1073/pnas.1604371113). They showed that single a2,3- and a2,6-linked sialic acid residues could be added to diverse therapeutic proteins, however it was only possible to add polySia to a domain of the natively polysialylated protein, neural cell adhesion molecule (NCAM).

The biosynthetic pathway used in this Example, depicted in FIG. 1, consists of four prokaryotic glycosyltransferases which act sequentially to build up polySia on a protein target in the bacterial cytoplasm. The glycosyltransferases in the pathway were chosen for their utility in the synthesis of free oligosaccharides in vivo and in vitro and for their acceptor substrate promiscuity. The chosen galactosyltransferase, LgtB of *N. meningitidis* (MC58), was used for initial extension of the N-linked glucose to form N-linked lactose (by linking galactose to the N-linked glucose). LgtB is known to transfer galactose onto diverse glucosides (see Lau et al., Chem. Commun. 46, 6066-6068 (2010)) but has never been tested with a protein- or peptide-linked acceptor. The N-linked lactose serves as a substrate for the bifunctional a2,3/a2,8 oligo-sialyltransferase from *Campylobacter jejuni*, CstII, which is capable of adding an a2,3 followed by up to three α2,8 linked Neu5Ac residues (see, e.g., Antoine et al., Angew. Chem. 117, 1374-1376 (2005); Blixt et al., Carbohydr. Res. 340, 1963-1972 (2005); and Gilbert et al., J. Biol. Chem. 275, 3896-3906 (2000)). Furthermore, the bifunctional sialyltransferase CstII is well established as the enzyme of choice for priming lactosides for extension by bacterial polysialyltransferases (Lindhout et al., Proc. Natl. Acad. Sci. U.S.A. 108, 7397-7402 (2011) and Antoine et al., Angew. Chem. 117, 1374-1376 (2005)). The specific CstII used was CstIIΔ32I53S from *C. jejuni* (OH4382/84), which has increased solubility, stability and α2,8 activity compared to the wild type protein (see Chiu et al., Nat. Struct. Mol. Biol. 11, 163-170 (2004)).

Disialyllactose can be extended by a polysialyltransferase (polyST). The polyST of *N. meningitidis* serogroup B can extend disialyllactose by more than one hundred α2,8-linked Neu5Ac residues (see Lindhout et al., Proc. Natl. Acad. Sci. U.S.A. 108, 7397-7402 (2011), Lindhout et al., PLoS ONE 8, e69888 (2013); and Freiberger et al., Mol. Microbiol. 65, 1258-1275 (2007)). The specific polyST used in the pathway generated in this Example was F116-polySTF460T from *N. meningitidis* serogroup B, which includes a total of 14 mutations, an N-terminal truncation of 25 amino acids, and an N-terminal Strep-tag that together increase the solubility and stability of the polyST and result in increased activity towards short oligosialic acid acceptors (see Keys et al., Nat. Chem. Biol. 10, 437-442 (2014); and Keys et al., Anal. Biochem. 427, 60-68 (2012)).

Each component of the biosynthetic pathway generated in this Example was incorporated into *E. coli* host cells, resulting in *E. coli* host cells that comprise relevant genes necessary to produce proteins (glycosyltransferases) involved in protein (poly)sialylation. Both, the bifunctional sialyltransferase CstII and polySTs require the activated donor sugar, CMP-Neu5Ac, in order to sialylate proteins. To ensure this substrate was produced by the host cells, a CMP-Neu5Ac synthetase, SiaB of *N. meningitidis* (MC58), was incorporated into the host cells and the media was supplemented with Neu5Ac that is taken up via the resident salvage pathway (see Antoine T et al. ChemBioChem 4, 406-412 (2003)).

The specific *E. coli* background used was *E. coli* K12 JM107ΔnanA:kan strain (see Priem et al., Glycobiology 12, 235-240 (2002)), which lacks β-galactosidase (LacZ) and sialic acid aldolase (NanA) activities which might otherwise degrade lactose and sialic acid respectively. In order to balance expression of the pathway enzymes and reduce metabolic load on the host strain, the genes encoding ApNGT, LgtB, CstII, polyST and SiaB were codon optimized (see Welch et al., PLoS ONE 4, e7002 (2009)), and ApNGT, LgtB, CstII, and SiaB were organized into a pseudo-operon (see Xu P. et al., ACS Synth. Biol. 1,256-266 (2012), Xu P. et al., Nat. Commun. 4, 1409 (2013), and He W. et al., Metab. Eng. 27 92-100 (2015)) with expression of each gene controlled by an inducible lacUV5 promoter (see Deuschle et al., EMBO J. 5, 2987-2994 (1986)) and a customized ribosome binding site (see Salis, H. M. in Methods in Enzymology (ed. Voigt, C.) 498, 19-42 (Academic Press, 2011)) designed to direct the initiation of translation at a moderate rate. See Table 1, construct pMA991. polyST was placed under control of the T5 promoter and a strong ribosome binding site. See Table 1, construct pMA1059.

The selected target protein to be (poly)sialylated in the host cell, containing Asn-X-Ser/Thr site(s), was placed under control of the pBAD promoter. See Table 1, constructs pMA885, pMA1045, and pLMTB3724.

6.3 Example 2: Glycosylation of a Homologous Protein: Polysialylated scAtaC

In this example scAtaC was selected as the target protein. scAtaC is a cytoplasmically retained, soluble fragment of the autotransporter adhesin from *A. pleuropneumoniae*, which is a native substrate of ApNGT, and which contains a high density of Asn-X-Ser(Thr) sites (see Naegeli et al., J. Biol. Chem. 289, 2170-2179 (2014)).

To test each step in the engineered glycosylation pathway, a series of constructs encoding glycosyltransferases involved in the synthesis of intermediate glycan structures was generated. These pathway constructs then were co-expressed with His6 tagged scAtaC. After culture, the modified target proteins were enriched and analyzed by SDS-PAGE and immunoblot. See FIG. 2. The successive addition of ApNGT, LgtB and CstII to the pathway resulted in successive increases in the apparent molecular mass of the target protein, suggesting that sialyllactose was added to the target protein.

To confirm that galactose and Neu5Ac were transferred onto N-linked glucose, a human serum, MS14, which detects the Glcβ1-Asn epitope, was used. When only ApNGT was co-expressed with the target protein, a prominent band was observed in the MS14 blot. See FIG. 2, lane 3. Addition of the downstream glycosyltransferases, LgtB and CstII, resulted in considerable masking of this epitope, indicating that N-linked glucose was the substrate for successive galactose and Neu5Ac transfer.

While the addition of ApNGT and LgtB to the pathway each resulted in a small increase to the apparent size of the target protein, addition of CstII resulted in a large increase in the apparent molecular mass and a broadening of the mass range. See FIG. 2, lane 5. A broad mass range is typical of glycoproteins and indicates the presence of different glycoforms. The different glycoforms likely result from varying site occupancy, and from varying amounts of sialylation by CstII, which adds up to three α2,8 linked Neu5Ac residues (see Blixt et al., Carbohydr. Res. 340, 1963-1972 (2005)). Importantly, deletion of ApNGT from the pathway abolished modification of the target protein, demonstrating that the galactose and Neu5Ac residues were transferred successively onto the priming N-linked glucose. See FIG. 2, lane 2.

To verify the presence of sialyllactose on the target protein, a LC-MS/MS was performed on enriched and trypsinized scAtaC samples. The modification of nine scAtaC peptides was observed, seven of which contained canonical Asn-X-Ser/Thr sites, and two peptides appeared to be modified at an alternative sequon. Eight of the nine sites were modified with mono-, di- or tri-sialyllactose. At the majority of sites the presence of glycosylation intermediates was observed. FIG. 3 shows the extracted ion chromatograms of one peptide for each intermediate from N-linked glucose to trisialyllactose and corresponding MS/MS spectra.

In a separate experiment, expression of the polyST (pMA1059) in combination with the remaining components of the sialyllactose pathway (pMA991), the synthesis of polysialic acid was observed. See FIG. 4, lane 3. In contrast, polysialic acid could not be detected in the absence of polyST expression (i.e., when only pMA991 was expressed). See FIG. 4, lane 2. Further, the amount of polysialic acid was dramatically reduced when plasmid pMA1075, which comprises LgtB, CstII, and SiaB, but not ApNGT was expressed with the polyST (pMA1059). See FIG. 4, lane 1.

To confirm that the target protein, scAtaC, was polysialylated, LC-MS/MS analysis was directly performed on the polysialic acid positive cell free extract. The results demonstrated the presence of polysialic acid chains of up to DP20 on scAtaC. The m/z species observed indicate both the presence of unmodified polysialic acid up to DP9, and polysialic acid chains with extensive intramolecular lactonization up to DP20. See Table 3. Lactonization is a reversible modification of polysialic acid occurring at low pH used for the LC-MS analysis and is not expected to exist at neutral pH. In addition to lactonization, extensive hydrolysis of polysialic acid can be expected at low pH, thus the length of polysaccharide observed in this analysis is likely to significantly underestimate the chain length synthesized on scAtaC. Nevertheless, polysialylation of scAtaC was clearly evident.

TABLE 3

LC-MS/MS analysis of a polysialylated scAtaC peptide
Peptide: K.GNLSTAADVTDK.N (v9 = 907.43)

| m/z | z | [M + H]+ | peptide [M + H]+ | glycan | structure |
|---|---|---|---|---|---|
| 758.35 | 2 | 1515.70 | 1191.59 | 324.11 | Hex2 |
| 903.90 | 2 | 1806.79 | 1191.59 | 615.21 | Hex2NeuAc |
| 1049.44 | 2 | 2097.89 | 1191.59 | 906.30 | Hex2NeuAc2 |
| 1194.99 | 2 | 2388.98 | 1191.59 | 1197.39 | Hex2NeuAc3 |
| 1340.54 | 2 | 2680.07 | 1191.59 | 1488.49 | Hex2NeuAc4 |
| 1486.09 | 2 | 2971.17 | 1191.59 | 1779.58 | Hex2NeuAc5 |
| 1631.64 | 2 | 3262.26 | 1191.59 | 2070.68 | Hex2NeuAc6 |
| 1777.18 | 2 | 3553.36 | 1191.59 | 2361.77 | Hex2NeuAc7 |
| 1922.73 | 2 | 3844.45 | 1191.59 | 2652.87 | Hex2NeuAc8 |
| 2068 28 | 2 | 4135.55 | 1191.59 | 2943.96 | Hex2NeuAc9 |

6.4 Example 3: Glycosylation of a Heterologous Protein: Polysialylated sfGFP In this Example the glycosylation of heterologous target proteins was demonstrated. Taking advantage of the short Asn-X-Ser(Thr) sequon, two superfolder green fluorescent protein (GFP) (Pedelacq et al., Nat. Biotechnol. 20, 927-932 (2002)) constructs were generated, with a single engineered glycosylation site. The glycosylation sites were added as a C-terminal tag or in a loop (between residues 194-195) to generate the "GlycoTag-" and "GlycoLoop-" constructs respectively. See FIG. 5a. Glucosylation was first probed by immunoblot using an N-Glc specific serum. See FIG. 5b. The results confirmed that both GFPs were glucosylated when co-expressed with the ApNGT. Quantitative MS analysis indicated approximately 86% and 97% glycosylation occupancy of the GlycoLoop- and GlycoTag-sites, respectively. In contrast, GFP constructs lacking a glycosylation site were not modified. It was also demonstrated that LgtB and CstII were able to extend the N-linked glucose to assemble the sialyllactose primer on the GlycoLoop-GFP by peptide LC-MS/MS. See FIG. 6.

In the following experiments the modified construct, GlycoTag-GFP, was used to test protein polysialylation. Bacterial polySTs require a minimum of disialyllactose to prime polysaccharide synthesis (Lindhout et al., Proc. Natl. Acad. Sci. U.S.A. 108, 7397-7402 (2002)). To test if the polymerase can extend the protein-linked sialyllactose primer, we co-expressed the entire polysialylation pathway (pMA991 and pMA1059) together with the GlycoTag-GFP construct (pMA1045) in JM107 ΔnanA:kan cells. Initially, we observed only a small amount of polySia, but optimization of shaker flask culture conditions considerably improved the yield and resulted in smearing of the GFP towards higher MW, suggesting modification of GFP with the polysaccharide. See FIG. 7. To confirm polysialylation, total GFP was purified via NiNTA affinity chromatography and the different glycoforms were separated via preparative anion exchange chromatography. See FIG. 8). The polysialylated GFP was expected to be retained on the column due to the negative charge carried by each sialic acid unit. In agreement with these expectations, the total GFP could be separated into three fractions which eluted in low, medium, and high salt, corresponding to GFP modified with no, oligo-, and poly-Sia respectively. See FIGS. 5c and d (polySia is defined here as chains of >10 residues). The precise length and distribution of polymers added to GFP was determined by analytical anion exchange chromatography of the intact glycoproteins. The polysialylated GFP fraction was modified with polymers comprising approximately 10 to 80 sialic residues in length, with the shorter chains being the most abundant. The α2,8-linkage of the polymer was confirmed by testing the sensitivity of the modification to digestion with endosialidase NF (Stummeyer et al., Nat. Struct. Mol. Biol. 12, 90-96 (2005)). Without further optimization, the biosynthetic pathway yielded 3 mg of polysialylated GFP from 1 liter of LB media, representing 5-10% of total GFP. Further improvements in the yield will be achieved by balancing expression of the pathway elements and improving the supply of CMP-Neu5Ac.

6.5 Example 4: Glycosylation of a Heterologous Protein: Polysialylated DARPin In this Example the polysialylation of a second heterologous target protein was tested. Homologous to the previous Example, the short Asn-X-Ser(Thr) sequon was added as a C-terminal tag to a potent VEGF-A-antagonistic designed ankyrin repeat protein (DARPin) (Stahl et al., Angiogenesis 16, 101-111 (2013)) to generate the GlycoTag-DARPin construct (pLMTB3724).

The entire polysialylation pathway (pMA991 and pMA1059) was co-expressed together with the GlycoTag-DARPin construct (pLMTB3724) in JM107 ΔnanA:kan cells.

Total DARPin was purified via NiNTA affinity chromatography and the different glycoforms were separated via preparative anion exchange chromatography. The polysialylated DARPin was expected to be retained on the column due to the negative charge carried by each sialic acid unit. In agreement with these expectations, the total DARPin could be separated into three fractions which eluted in low, medium, and high salt, corresponding to DARPin modified with short, medium, and long polySia chains, respectively. See FIG. 9a.

The purified proteins were analyzed using High Performance Size Exclusion Chromatography (HPSEC). The chromatograms of unglycosylated DARPin, which was produced in JM107 ΔnanA:kan cells lacking protein glycosylation machinery, and the different polysialylated DARPin preparations are shown in FIG. 9b. Using a gel filtration standard, the molecular weight (MW) of the polysialylated species was determined. The MW of the glycoproteins determined by HPSEC was significantly higher compared to protein size estimation using SDS-PAGE, which is mainly due to the polyanionic nature of the polySia chain that drastically increases the hydrodynamic volume of the glycoprotein. See Table 4.

In a surface plasmon resonance (SPR) study, the binding properties and kinetics of the different DARPin preparations' interactions with $VEGF_{165}$ were analysed and compared to the VEGF receptor's (recombinant human VEGF-$R_1$) interactions with $VEGF_{165}$. For determination of the kinetic parameters, the concentration of the probe was measured using a BCA assay (Pierce) and the molecular weight was determined via the SPR signal measured at saturating conditions ($R_{max}$). See Table 4 for the MW determined via SPR. Each probe was measured twice on sensor surfaces with three different densities of covalently immobilized recombinant human $VEGF_{165}$. The kinetic constants of the measurements are summarized in Table 5. The $K_D$ of rhVEGF-R1 is in the double-digit nanomolar range. The unmodified DARPin has a single-digit picomolar affinity to human $VEGF_{165}$, as reported by Stahl et al. (Angiogenesis 16, 101-111 (2013)). Importantly, modification with polysialic acid does not decrease the affinity of DARPin to VEGF as all DARPin preparations have similar $K_D$ values.

TABLE 4

Molecular weight determination of unglycosylated and polysialylated DARPin preparations by SDS-PAGE, HPSEC and SPR.

| Sample | $MW_{SDSPAGE}$ (kDa) | $MW_{SEC}$ (kDa) | $MW_{SPR}$ (kDa) |
|---|---|---|---|
| DARPin | 15-20 | 17.6 | 17.6 |
| DARPin$_{short\ polySia}$ | 25-35 | 44 | 24.6 |
| DARPin$_{mid\ polySia}$ | 25-50 | 158 | 35.2 |
| DARPin$_{long\ polySia}$ | 30-170 | 500 | 54.6 |

TABLE 5

Kinetic constants of VEGF binding proteins (DARPins and VEGF receptor) binding to $VEGF_{165}$.

| Sample | $k_a$ (M$^{-1}$s$^{-1}$) | $k_d$ (s$^{-1}$) | $K_D$ (M) |
|---|---|---|---|
| rhVEGF-R1 | 1.1 (±0.3) × 10$^6$ | 8.1 (±3.5) × 10$^{-5}$ | 6.9 (±1.6) × 10$^{-11}$ |
| DARPin | 2.9 (±0.7) × 10$^7$ | 9.9 (±6.8) × 10$^{-5}$ | 3.3 (±3.1) × 10$^{-12}$ |
| DARPin$_{short\ polySia}$ | 1.7 (±0.2) × 10$^7$ | 1.2 (±0.3) × 10$^{-4}$ | 7.0 (±2.3) × 10$^{-12}$ |
| DARPin$_{mid\ polySia}$ | 2.1 (±0.3) × 10$^7$ | 1.0 (±0.5) × 10$^{-4}$ | 5.2 (±3.4) × 10$^{-12}$ |
| DARPin$_{long\ polySia}$ | 2.2 (±0.5) × 10$^7$ | 8.7 (±4.2) × 10$^{-5}$ | 4.4 (±2.7) × 10$^{-12}$ |

6.6 Example 5: Generation of a Host Cell Capable of Cytosolic Protein Glycosylation: Engineering a Pathway for De Novo Biosynthesis of CMP-Neu5Ac In previous Examples, the endogenous scavenger pathway for CMP-Neu5Ac biosynthesis was utilized to produce precursors for glycosylation of a target protein. This pathway takes advantage of the fact that E. coli is able to catabolize Neu5Ac and possesses a sialic acid permease, NanT. However, up to one hundred equivalents of CMP-Neu5Ac are required for polysialylation of a single protein as the $K_M$ of bacterial polySTs for CMP-Neu5Ac is relatively high, in the range of 1-5 mM (Lindhout et al. PLos One 8 2013 doi: 10.1371/journal.pone.0069888). Therefore, the donor molecule, CMP-Neu5Ac, could be a limiting reagent for the biosynthesis of polysialylated proteins.

In this Example a de novo pathway for CMP-Neu5Ac synthesis was introduced into the E. coli K12 derivative W3110 in order to boost the endogenous pool of the donor molecule CMP-Neu5Ac. The strategy used involved deletion of the genomically encoded Neu5Ac catabolic enzymes (nanAK), and heterologous expression of the CMP-Neu5Ac biosynthetic enzymes siaABC from Neisseria meningitidis serogroup B (see FIG. 1, Keys et al. Anal Biochem. 427, 60-68 (2012), Fierfort and Semain J Biotechnol. 134, 261-5 (2008), and Richard et al. Glycobiology. 26, 723-31 (2016)). The siaABC genes occur as part of a polycistronic operon encoding biosynthesis of the polysialic acid capsule in Neisseria meningitidis serogroup B. These genes were taken as a block, together with their native RBSs, placed behind an inducible promoter (lacUV5), and introduced into the "sialyllactose pathway" construct giving rise to pLMTB4250. See Table 1.

To test if the de novo pathway for CMP-Neu5Ac biosynthesis was functional, glycosylation pathway constructs were co-expressed together with the GlycoTag-GFP construct (pMA1045) in StLMTB10758 (W3110 ΔlacZ ΔnanA ΔnanK). Total GFP was enriched via NiNTA beads and the samples were analysed by SDS-PAGE followed by Coomassie staining. See FIG. 10. Polysialylation was probed by immunoblot using a polySia specific monoclonal antibody. The results confirmed that GFP was polysialylated when co-expressed with pLMTB4250, i.e. expressing the sialyllactose pathway including the N. meningitidis serogroup B genes for the de novo synthesis of CMP-Neu5Ac (siaABC), and the polyST (pMA1059). See FIG. 10, lane 2. A weaker polySia signal was detected in enriched GFP samples produced in host cells using the scavenger pathway for CMP-Neu5Ac biosynthesis, i.e. cell cultures that have been supplemented with Neu5Ac and expressing only siaB. See FIG. 10, lane 4. Co-expression with pLMTB4250 resulted in an increase in the apparent molecular mass of GlycoTag-GFP, suggesting that sialyllactose was added to the target protein. See FIG. 10, lane 1. As expected, no polySia was detected when GlycoTag-GFP was purified from host cells expressing no glycosylation pathway. See FIG. 10 lane 3.

6.7 Example 6: Generation of a Host Cell Capable of Cytosolic Protein Glycosylation: In Vivo Polysialylation of Target Proteins Using polyST Homologs In previous Examples, the polyST from N. meningitidis serogroup B was used for in vivo polysialylation of target proteins. The specific variant used, F116-polyST$_{F460T}$, includes a total of 14 mutations, an N-terminal truncation of 25 amino acids, and an N-terminal Strep-tag. Together these modifications increase the solubility and stability of the polyST and result in increased activity towards short oligosialic acid acceptors (see Keys et al., Nat. Chem. Biol. 10, 437-442 (2014); and Keys et al., Anal. Biochem. 427, 60-68 (2012)). This example demonstrates that polyST homologs can substitute for F116-polyST$_{F460T}$ in the engineered pathway for protein polysialylation. A novel polyST from Mannheimia haemolytica has recently been described that combines several favourable biochemical properties (see Lindhout et al., PLoS One 2013 8(7):e69888. doi: 10.1371/journal.pone.0069888). Accordingly to previous Examples, the polyST from Mannheimia haemolytica, containing an N-terminal deletion of 20 amino acids (Δ20polyST$_{Mh}$), was cloned into pCDF-DUET expression plasmid with or without an N-terminal maltose-binding-protein fusion. See pLMTB3961 and pLMTB3962 in Table 1, respectively. To test if the Δ20polyST$_{Mh}$ variants can extend the protein-linked sialyllactose primer, the entire polysialylation pathway was co-expressed together with the GlycoTag-GFP construct (pMA1045) in StLMTB10758 (W3110 ΔlacZ ΔnanA ΔnanK). Total GFP was enriched via NiNTA beads and the samples were analysed by SDS-PAGE followed by immunoblot with an anti-polySia specific monoclonal antibody. See FIG. 11a. The results confirmed that GlycoTag-GFP was polysialylated when co-expressed with Δ20polyST$_{Mh}$ constructs (either pLMTB3961 or pLMTB3962) together with pLMTB4250. See FIG. 11a, lane 3 and 4. As expected, no polySia signal was detected in an enriched GFP sample produced in host cells expressing no glycosylation pathway. See FIG. 11a, lane 1. Co-expression with the sialyllactose pathway (pLMTB4250) resulted in an increase in the apparent molecular mass of GlycoTag-GFP, suggesting that sialyllactose was added to the target protein. See FIG. 11a, lane 2. The precise length and distribution of polymers added to GFP was determined by analytical anion exchange chromatography of the intact glycoproteins. See FIG. 11b. Co-expression with the sialyllactose pathway (pLMTB4250) resulted in the assembly of short oligosialic acids up to DP4, which is in agreement with the reported activity of CstII (see Blixt et al., Carbohydr. Res. 340, 1963-1972 (2005)). Polysialylated GFP was detected upon co-expression of the entire polysialylation pathway (pLMTB4250 and pLMTB3961/pLMTB3962). Without further optimization, the biosynthetic pathway including Δ20polyST$_{Mh}$ construct (pLMTB3961) resulted in the modification of 20-25% of total GFP with polysialic acid (defined as DP10).

6.8 Conclusions

These Examples demonstrate that glycosyltransferases co-expressed in the E. coli cytosol are able to use N-linked glucose as a primer for protein glycosylation. In particular, these Examples demonstrate that a synthetic polysialylation pathway can be generated that, when expressed in E. coli, results in polysialylation of target proteins. This finding is extremely important, as it allows for use of host cells (such E. coli) to generate polysialylated proteins (such as therapeutic proteins) with extended half-lives relative to their non-polysialylated counterparts.

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

---

What is claimed is:

1. A host cell comprising (i) a heterologous nucleic acid that encodes a target protein comprising an N-glycosylation consensus sequence of the formula Asn-X-Ser(Thr), wherein X can be any amino acid residue except Pro; (ii) a nucleic acid that encodes a heterologous N-glycosyltransferase (NGT) that adds glucose to an amino acid residue present in said N-glycosylation consensus sequence; (iii) a nucleic acid that encodes a heterologous galactosyltransferase that catalyzes addition of a galactose to said glucose; (iv) a nucleic acid that encodes a heterologous sialyltransferase; (v) a nucleic acid that encodes a heterologous polysialyltransferase (polyST); and (vi) a nucleic acid that encodes a heterologous CMP-Neu5Ac synthetase; wherein the host cell is capable of glycosylating the target protein at the N-glycosylation consensus sequence with glucose-galactose primer and polysialylation.

2. The host cell of claim 1, wherein said heterologous NGT is the NGT of *Actinobacillus* pleuropneumonias, the NGT of a species of *Haemophilus*, the NGT of a species of *Mannheimia*, the NGT of a species of *Bibersteinia*, or the NGT of a species of *Yersinia*.

3. The host cell of claim 1, wherein said heterologous galactosyltransferase is LgtB of *Neisseria meningitidis*, the LgtB of *Neisseria gonorrhoeae*, LgtE of *Neisseria meningitidis*, CgtB of *Campylobacter jejuni*, WaaX of *Escherichia coli*, HP0826 of *Helicobacter pylori*, or a eukaryotic β4Gal-T1.

4. The host cell of claim 1, wherein said heterologous sialyltransferase is CstII of *Campylobacter jejuni*, CstI of *Campylobacter jejuni*, Lst of *Neisseria meningitidis*, or Lst of *Neisseria gonorrhoeae*.

5. The host cell of claim 1, wherein said heterologous poly ST is a poly ST of *Neisseria meningitidis* or a homolog thereof, *Escherichia coli* K1 or a homolog thereof, *Mannheimania haemolytica* or a homolog thereof, or *Moraxella nonliquifacien* or a homolog thereof.

6. The host cell of claim 1, wherein said heterologous CMP-Neu5Ac synthetase is SynB of *Neisseria meningitidis*.

7. The host cell of claim 1, wherein said host cell is a prokaryotic host cell or eukaryotic host cell.

8. The host cell of claim 1, wherein said target protein is a bacterial protein, eukaryotic protein, or therapeutic protein.

9. The host cell of claim 1, wherein said host cell does not comprise an oligosaccharyltransferase (OST).

10. A method for producing a glycosylated target protein that comprises a glucose assembled at an amino acid residue present in an N-glycosylation consensus sequence; wherein said glucose is linked to a monosaccharide, said method comprising (i) culturing the host cell of claim 1 under conditions suitable for protein production and (ii) isolating said target protein.

11. A method for producing a sialylated target protein, comprising (i) culturing the host cell of claim 1 under conditions suitable for protein production and (ii) isolating said sialylated target protein.

12. A method for producing a polysialylated target protein, comprising (i) culturing the host cell of claim 1 under conditions suitable for protein production and (ii) isolating said polysialylated target protein.

13. A kit comprising the host cell of claim 1.

\* \* \* \* \*